(12) United States Patent
Kolpashchikov

(10) Patent No.: US 8,313,903 B2
(45) Date of Patent: Nov. 20, 2012

(54) BINARY DNA PROBE FOR FLUORESCENT ANALYSIS OF NUCLEIC ACIDS

(75) Inventor: Dmitry Kolpashchikov, Winter Park, FL (US)

(73) Assignee: The Trustees of Columbia University in the City of New York, New York, NY (US)

(*) Notice: Subject to any disclaimer, the term of this patent is extended or adjusted under 35 U.S.C. 154(b) by 479 days.

(21) Appl. No.: 12/295,625

(22) PCT Filed: Apr. 1, 2007

(86) PCT No.: PCT/US2007/065744
§ 371 (c)(1),
(2), (4) Date: Sep. 30, 2008

(87) PCT Pub. No.: WO2007/115242
PCT Pub. Date: Oct. 11, 2007

(65) Prior Publication Data
US 2009/0176318 A1    Jul. 9, 2009

Related U.S. Application Data

(60) Provisional application No. 60/788,029, filed on Mar. 31, 2006, provisional application No. 60/793,481, filed on Apr. 20, 2006.

(51) Int. Cl.
*C12Q 1/68* (2006.01)
*C07H 21/04* (2006.01)

(52) U.S. Cl. ...................... 435/6.1; 536/24.32

(58) Field of Classification Search ............ 536/23.1, 536/24.3, 24.32; 435/6, 6.1
See application file for complete search history.

(56) References Cited

U.S. PATENT DOCUMENTS

| 6,686,157 | B2 * | 2/2004 | Ward et al. ............... 435/6.1 |
| 2003/0129611 | A1 * | 7/2003 | Bao et al. ................. 435/6 |
| 2005/0042638 | A1 * | 2/2005 | Arnold et al. ............. 435/6 |
| 2007/0231810 | A1 |  10/2007 | Todd et al. |

FOREIGN PATENT DOCUMENTS

| WO | WO 0040751 A2 | 7/2000 |
| WO | 03000933 | 1/2003 |
| WO | WO 2007/115242 A2 | 10/2007 |

OTHER PUBLICATIONS

Bichenkova, E. et al., Target-assembled tandem oligonucleotide systems based on exciplexes for detecting DNCA mismatches and single nucleotide polymorphisms, journal, May 2005, pp. 956-964, Elsevier.
Li, Q., A new class of homogeneous nucleic acid probes based on specific displacement hybridization, journal, Aug. 2001, pp. 1-9, vol. 30, No. 2, Oxford University Press.
Supplementary European Search Report, Application No. 07759922.3-1222/2013561, Nov. 23, 2009.
International Search Report and Written Opinion, PCT/US 09/654341, Nov. 20, 2009, pp. 1-10.
Kolpashchikov, D., Split DNA Enzyme for Visual Single Nucleotide Polymorphism Typing, journal, Jacs Communication, Dec. 17, 2007, pp. 2934-2935, vol. 130, No. 10, American Chemical Society, United States.
International Search Report and Written Opinion for PCT/US07/61583, dated Feb. 26, 2008, pp. 1-12.
International Search Report and Written Opinion for PCT/US07/65744, dated Sep. 2, 2008, pp. 1-11.
Muller., IEE Proc Nannobiotechnology, Apr. 2006, vol. 153, No. 2, 31-40.
Amontov, et al., J. Am. Chem. Society, 1996, vol. 118, 1624-28.
Wang, et al., J. Mol. Biol. 2001, vol. 310-, 723-34.
Todd AV, et al. Clin Chem. May 2000;46(5):593-4).
Macdonald J, et al. Methods Mol Biol. 2006;335:343-63.
Kolpashchikov D.M., Stojanovic M.N. (2005) "Boolean control of aptameric binding states." JACS, 127, 11348-11341.
Kolpashchikov D.M. (2005) Binary malachite green aptamer for fluorescent detection of nucleic acids. JACS, 127, 12442-12443.
Tyagi,S., et al. (1996) Nat. Biotechnol. 14, 303-308; 15.
Levy, M., Ellington, A. D. 2003 Proc Natl Acad Sci U S A. 100:6416-6421.
Tyrrell, J. V. and Bergquist, P. R. New Zealand Journal of Marine and Freshwater Research, 1997, vol. 31:551-560.
Bonnet,G., et al. (1999) Proc. Natl. Acad. Sci. U. S. A. 96, 6171-6176.
Marras,S.A., et al. (2006) Clin. Chim. Acta. 363, 48-60.
EPO, "European Office action for corresponding EP application No. 07 759 922.3-1222", Mar. 25, 2011, pp. 17.
Kolpashchikov, Dmitry M., "A Binary DNA Probe for Highly Specific Nucleic Acid Recognition", "J. Am. Chem. Soc.", Jul. 21, 2006, pp. 10625-10628, vol. 128, Publisher: American Chemical Society, Published in: US.
W. Tan, et al., "Abstract of Abberant miRNA methylation in tumors from surgically resected lung cancer patients and association", "AACR 101st Annual Meeting 2010", 2010, pp. 1-1, Publisher: American Association for Cancer Research, Published in: Philadelphia/USA.
USISA, "European Search Report for the corresponding EP12163344", pp. 19, Publisher: European Patent Office, Published in: Netherlands.

* cited by examiner

*Primary Examiner* — Gary Benzion
*Assistant Examiner* — Cynthia Wilder
(74) *Attorney, Agent, or Firm* — Evans & Molinelli PLLC; Judith A. Evans

(57) ABSTRACT

The invention is directed to binary oligonucleotide probes for nucleic analysis, which probes can be made of DNA or RNA that recognize nucleic acid analytes (both DNA and RNA) with unprecedented high selectivity under mild conditions and are highly sensitive to single nucleotide mismatches (SNP single nucleotide polymorphisms) without PCR amplification. In one group, the binary probes indicate that they have hybridized to a particular nucleic analyte by binding to a molecular beacon that gives off a fluorescent signal. A second group of binary probes bind to a dye such as malachite green, where upon hybridization to analyte the fluorescence of the dye increases dramatically and is easily detected and measured. The new binary probes require only about five minutes at room temperature to generate a detectable signal.

42 Claims, 15 Drawing Sheets though none effectively combine high sensitivity with mild conditions. Therefore, there is a need for probes that reliably detect single nucleotide mismatches (Single Nucleotide Polymorphisms, SNP) under milder or physiologic conditions.

BINARY DNA PROBE FOR FLUORESCENT ANALYSIS OF NUCLEIC ACIDS

CROSS REFERENCE TO RELATED APPLICATIONS

This application claims benefit of Provisional Application 60/793,481, filed on Apr. 20, 2006, and Provisional Application 60/788,029, filed on Mar. 31, 2006, which are incorporated herein by reference, under 35 U.S.C. §119(e).

STATEMENT OF GOVERNMENTAL INTEREST

This invention was made with Government support under NIH, NIBIB, RO1 EB000675, NSF, NHGRI R21 HG004060, and BES 0321972 (PI M. N. S.). The Government has certain rights in the invention.

BACKGROUND OF THE INVENTION

1. Field of the Invention

The present invention relates to binary probes for fluorescent analysis of nucleic acids using molecular beacons or dyes.

2. Description of the Related Art

Sequence-specific detection of nucleic acids is crucial to disease diagnosis, genome study, and mRNA monitoring in living cells. Among the numerous methods for nucleic acid analysis are those that provide an immediate visible or fluorescent response after hybridization of the probe to complementary nucleic acid analytes. This offers easy and instant detection of the specific DNA and RNA analyte. However, the selectivity and efficacy of known methods is limited under physiological conditions, and this limitation hinders using the probes in living cells.

Numerous techniques for DNA and RNA analysis such as fluorescence in situ hybridization, micro-array technology, the molecular beacon approach and others rely on the ability of the probe to recognize DNA and RNA analytes in a sequence specific manner by forming duplexes. The formation of 16-20 nucleotide hybrids between probe and nucleic acid analyte is required in order to uniquely define a specific fragment in DNA the size of a genome. However, 16-20 nucleotide hybrid duplexes are too stable to be sensitive to a single mismatch at mild conditions. A number of different strategies have been developed in an attempt to solve this problem, however none effectively combine high sensitivity with mild conditions. Therefore, there is a need for probes that reliably detect single nucleotide mismatches (Single Nucleotide Polymorphisms, SNP) under milder or physiologic conditions.

BRIEF DESCRIPTION OF THE DRAWINGS

The present invention is illustrated by way of example, and not by way of limitation, in the figures of the accompanying drawings and in which like reference numerals refer to similar elements.

SUMMARY OF THE INVENTION

Figure 1:
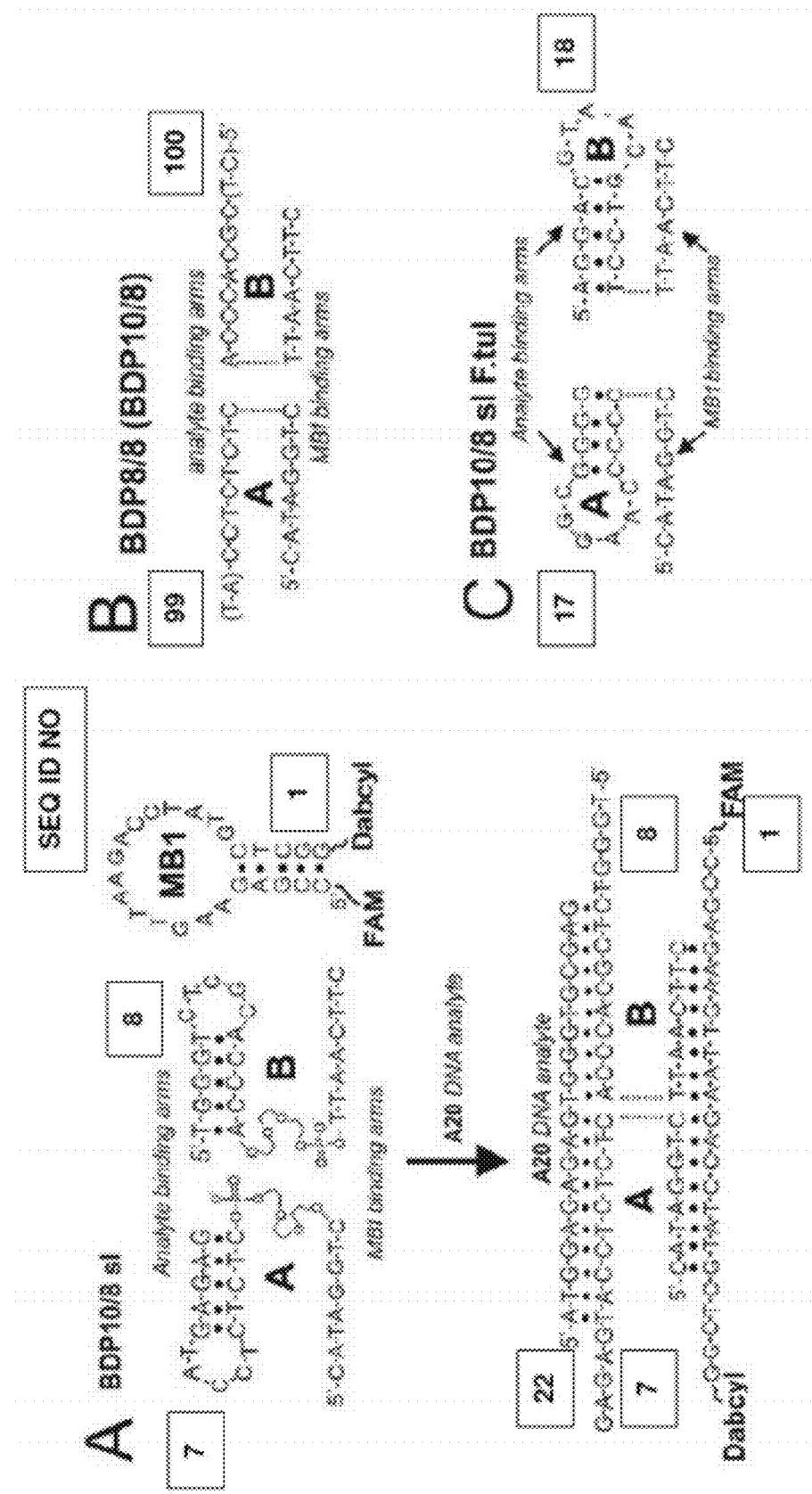
FIG. 1 Primary and secondary structure of binary DNA probes (BDPs) used in the present study A: Structure of BDP 10/8sl in the absence (top) or presence (bottom) of A20 DNA analyte. B: Structure of strands A and B of BDP8/8 and BDP10/8. C: Structure of strands A and B of BDP10/8sl F. tul. The triethylene glycole linkers are depicted by the dashed lines on the panels A (bottom), B and C.

One set of embodiments is directed to non-naturally occurring binary oligonucleotide probes for detecting a single stranded oligonucleotide analyte comprising two antiparallel oligonucleotide strands, wherein 1. a first oligonucleotide strand has a. at its 5'-terminus a molecular beacon binding arm that is complementary to and selectively hybridizes with a molecular beacon, and B. that is flanked by a linker that is flanked by a first oligonucleotide analyte binding arm, and c. at its 3'-terminus, the first oligonucleotide analyte binding arm that is complementary to and selectively hybridizes with a first region of the oligonucleotide analyte; and 2. a second oligonucleotide strand that is antiparallel to the first. The analyte binding arm can be DNA or RNA and is from 6-20 nucleotides long; the linkers are any molecule that is flexible enough to let the probe form a double helix when analyte is bound to the analyte binding arms. The molecular beacon-binding arms are typically from 4-20 nucleotides long, but can be longer and are customized to bind to a particular molecular beacon in such a way that the fluorophore and quencher are separated when the probe is bound to analyte. The binary probe can be designed to hybridize with any molecular beacon known in the art. The probe can be customized to hybridize with a DNA, RNA or chimeric analyte, and can be made more stable by adding stem loop structures to the ends of the first and second strands.

One set of embodiments is directed to a binary oligonucleotide probe hybridization assay to detect a single stranded nucleotide analyte having a known sequence in a sample containing a heterogeneous mixture of nucleic, having the following steps: a) providing a first binary oligonucleotide probe described in claim 1, wherein the nucleotides in the analyte binding arms of the first probe are complementary to the known nucleotide sequence in the first analyte, b) providing a first molecular beacon that fluoresces at a first wavelength and that selectively hybridizes to the molecular beacon binding arms on the first probe, c) creating a mixture comprising the first binary probe and the first molecular beacon, d) determining a first background level of fluorescence of the first molecular beacon for the mixture of step c, e) adding the sample to the mixture of step c, f) maintaining said mixture of step e for a sufficient period of time and under predetermined reaction conditions to allow the analyte to hybridize to the analyte binding arms on the first probe, and for the first molecular beacon to hybridize to the molecular beacon binding arms on the first probe, then, g) determining that the analyte is present in the sample if the level of fluorescence of the first molecular beacon increases above the first background level. The assay can use more than one different probe that are each customized to bind to a particular analyte and molecular beacon so that more than one analyte in a mixture can be analyzed in a single assay.

Another set of embodiments are directed to nucleic acid assay kits that include the customized probe and molecular beacon. Other kits include a molecular beacon and a truncated probe having the molecular beacon-binding arm with or without a linker so that the user can add the analyte binding arm of choice.

Another set of embodiments is directed to non-naturally occurring binary oligonucleotide probes for detecting a single stranded oligonucleotide analyte, the probe comprising two antiparallel oligonucleotide strands, wherein the first strand has a) at its 5'-terminus an analyte binding arm, flanked by a linker, b) the linker that is flanked by a first stem sequence, c) the first stem sequence that is complementary to a first stem sequence on the second strand, and that is flanked by a dye-binding nucleotide sequence, d) the dye-binding nucleotide sequence that is flanked by a second stem sequence, and e) at its 3'-terminus the second stem sequence that is complementary to a second stem sequence on the second strand, and a second oligonucleotide strand that is antiparallel to the first. These probes can be made of DNA or RNA, and can be varied as described above for the molecular beacon-binding probe. Other embodiments are directed to a nucleic acid assay using the dye-binding probes, and to kits containing a customized probe and dye, or a truncated probe that the user can customize.

Another set of embodiments is directed to non-naturally occurring fluorescent oligonucleotide tandem probes for a detecting single nucleotide polymorphism in a single stranded oligonucleotide target analyte that have: a) a first oligonucleotide strand bound to a quencher, wherein the first strand is complementary to a first region in the analyte, b) a second oligonucleotide strand bound to a fluorophore, wherein the second strand is complementary to a second region in the analyte, and c) wherein the first and second strands are separated by a five nucleotide gap when hybridized to the target analyte, which gap contains the single nucleotide polymorphism. In some embodiments the gap is 4-7 nucleotides long.

Another set of embodiments is directed to a method for identifying an SNP in an analyte nucleotide fragment, using the fluorescent oligonucleotide tandems. This assay has the steps of: 1. identifying a known SNP in a chromosome in the genome of an animal, 2. obtaining an single stranded analyte fragment from human or an experimental animal which fragment comprises a part of the chromosome having the known SNP identified in step 1, 3. identifying a nucleotide long target analyte sequence in the analyte fragment, in which the position of the known SNP is at the center (the number 3 nucleotide), 4. designing a fluorescent oligonucleotide tandem probe that binds to the target analyte, 5. designing four oligonucleotides from 4-7 nucleotides long of known sequence in which the nucleotides in all positions except one are complementary to respective nucleotides in the target sequence, 6. mixing the analyte with the first and second oligonucleotide probes under conditions that permit hybridization, 7. determining the amount of fluorescence in the mixture of step 6, to obtain a baseline fluorescence, 8. adding one of the four penta-oligonucleotides probes under conditions that permit hybridization, 9. measuring the fluorescence of the mixture in step 8, 10. determining that a penta-oligonucleotide has bound to the target sequence and is fully complementary to the target sequence if the fluorescence determined in step 9 is significantly greater than the baseline fluorescence, 11. if the penta-oligonucleotide of step 10 is determined to be fully complementary to the target sequence, then identifying the nucleotide at the center position of the target sequence as that corresponding to the nucleotide at the center position of the penta-nucleotide added in step 6, and 12. determining whether the nucleotide at the center position of the target sequence represents an SNP by comparing it with the known SNP, and 13. if the penta-oligonucleotide is not fully complementary to the target sequence, then washing out the penta-oligonucleotide and adding another penta-oligonucleotide before repeating steps 8-12.

DEFINITIONS

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G (as well as U) may occasionally participate in base pairings. Nucleotides that normally pair up when DNA or RNA adopts a double stranded configuration may also be referred to herein as "complementary bases".

"Complementary nucleotide sequence" here generally refers to a sequence of nucleotides in a single-stranded molecule or segment of DNA or RNA that is sufficiently complementary to that on another single oligonucleotide strand to specifically hybridize to it with consequent hydrogen bonding. Where single nucleotide polymorphisms are the target for detection, then the complementarity between the analyte and analyte-binding arm on the binary probes should be exact, 100%. If less selectivity is required, then routine experimentation will determine the level of complementarity that provides the desired result.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a "nucleoside". When the nucleoside contains a phosphate group bonded to the 3' or 5' position of the pentose, it is referred to as a nucleotide. A sequence of nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different or unusual sugars (i.e. sugars other than the "usual" pentose), or a combination of the two. Nucleotide analogs of DNA or RNA can be used to make binary probes. Examples of nucleotide analogs useful according to the present invention include those listed in the approved listing of modified bases at 37 CFR .sctn.1.822 (which is incorporated herein by reference). Other useful analogs include those described in published international application no. WO 92/20823 (the disclosures of which are incorporated herein by reference), or analogs made according to the methods disclosed therein.

"Oligonucleotide or polynucleotide" generally refers to a polymer of single-stranded nucleotides. As used herein, "oligonucleotide" and its grammatical equivalents will include the full range of nucleic acids. An oligonucleotide will typically refer to a nucleic acid molecule comprised of a linear strand of deoxy- and ribonucleotides.

In various embodiments, the binary probe of the present invention may combine one or more modifications or mutations including additions, deletions, and substitutions. These mutations may, for example, change the length of, or alter the nucleotide sequence of, a loop, a spacer region or a recognition sequence (or domain). Modification or mutation of the recognition site via well-known methods allows one to alter the sequence specificity of an enzymatic nucleic acid molecule.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35 40° C., with 37° C. being particularly preferred, as well as a pH of about 7.0 8.0, with 7.5 being particularly preferred, and further comprise the availability of cations, preferably divalent and/or monovalent cations, with a concentration of about 2 15 mM $Mg^{2+}$ and 0 1.0 M $Na^+$ being particularly preferred

DETAILED DESCRIPTION

Various embodiments of the present invention are directed to new binary oligonucleotide probes that can be made of DNA or RNA, which recognize nucleic acid analytes (both DNA and RNA) with unprecedented high selectivity under mild conditions and are highly sensitive to single nucleotide mismatches (SNP single nucleotide polymorphisms) without PCR amplification. In one group, the binary probes indicate that they have hybridized to a particular nucleic analyte by binding to a molecular beacon that gives off a fluorescent signal. A second group of binary probes bind to a dye such as malachite green, where upon hybridization to analyte the fluorescence of the dye increases dramatically and is easily detected and measured. The new binary probes require only about five minutes at room temperature to generate a detectable signal.

Certain other embodiments include various kits that include the binary probe oligonucleotides customized to bind to a nucleic acid analyte of interest, and the molecular beacon. These probes can be used to detect clinically significant nucleic acids such as those indicating a viral or bacterial infection or a cancer antigen. Other embodiments are directed to products and an assay called the fluorescent oligonucleotide tandem (FOT) assay, which allows fluorescent analysis of SNPs in nucleic acid analytes at room temperature using fluorophore- and a quencher-conjugated oligonucleotides that hybridize to analyte DNA or RNA. Like the binary probes, FOT probes can be made of either DNA or RNA. The FOT assay can be adapted for high throughput assays of nucleic acids using microchip technology.

In the following description, for the purposes of explanation, numerous specific details are set forth in order to provide a thorough understanding of the present invention. It will be apparent, however, to one skilled in the art that the present invention may be practiced without these specific details.

Binary Oligonucleotide Probe Design

The basic binary probe of the present invention is made of two synthetic, non-naturally occurring, anti-parallel oligonucleotide strands that can be made of DNA or RNA or a combination of both. Each strand of the DNA or RNA probe has a customized fragment that is complementary to a selected target nucleic acid analyte (analyte-binding arm), and a customized fragment complementary to a reporter such as a molecular beacon or a dye such as malachite green. The analyte binding and reporter binding arms are connected to each other by linker molecules that are either added between the two arms, or the linker includes one or more nucleotides that are part of the analyte and reporter binding arms themselves. For additional sensitivity, preferred embodiments of the binary probes have additional nucleotide sequences added to one or both of the free ends of each strand of the probe that are complementary to and hybridize with an internal region of the respective strand to form a stem-loop structure. These additional stem-loop-forming sequences are called structure stabilization arms (SSA), and will be discussed in more detail below.

Binary DNA Probes that Bind Molecular Beacons

The newly discovered binary probes have two separate, antiparallel DNA or RNA strands. The binary DNA probe is referred to herein as the BDP. The basic probe has several distinct regions on each strand: an analyte-binding arm flanked by a flexible linker that is flanked by a molecular beacon-binding arm that binds to a molecular beacon to indicate that the analyte has been detected. These probes are called "binary" because the two parts of the probe act synergistically and the detection event occurs only when both strands (FIGS. 1A and B) are hybridized to the analyte. In the absence of a nucleic acid analyte, the strands are dissociated and the probe does not bind the molecular beacon. Addition of a specific DNA/RNA analyte, some or all of which is complementary to the respective analyte-binding arms on the two halves of the probe, results in hybridization of the analyte-binding arms to the corresponding complementary nucleotides on the analyte. The analyte can and often is longer than the combined length of the two analyte-binding arms on the binary probe. When the analyte binds to the probe, the two strands of the probe come together and bind through the molecular beacon-binding arms to a molecular beacon, thereby generating a signal (fluorescence or dye marker) indicating that the analyte has been detected.

In the most basic form of the molecular beacon (MB)-binding BDP, the first strand (A in the figures) has a. at its 5'-terminus a MB binding arm that is complementary to and selectively hybridizes with a first nucleic acid sequence in a MB (a molecular beacon). The MB binding arm is flanked by a flexible linker, b. a flexible linker that is flanked by a first oligonucleotide analyte-binding arm and c. a first oligonucleotide analyte-binding arm that is complementary to and selectively hybridizes with a first region of an oligonucleotide analyte.

The second strand is antiparallel to the first.

The analyte-binding arms are customized for each particular analyte. In the examples the probe is entirely DNA, but it can be made of RNA or be a chimera. Likewise the analyte can be DNA, RNA or a chimera. The MB binding arms are customized to complement and hybridize with nucleotide fragments or sequences in any molecular beacon known in the art. For optimum selectivity, for example of SNPs, the analyte-binding arm of each strand of the probe ranges from 6-20 nucleotides in length, preferably 10, which make total recognizable analyte fragment 12-40 nucleotides long. A variant of the binary probe that can recognize a 20 nucleotide analyte and contains 10 nucleotide long analyte-binding arms in both strands is the BDP10/8sl (FIG. 1A). Analyte-binding arms of 10 nucleotides are preferred because a combined length of 20 nucleotides will cover any unique sequence in the genome. The binary probe BP8/8 has two 8 nucleotide long analyte-binding arms; therefore it is capable of recognizing 16 nucleotides of a nucleic acid analyte. Analyte-binding arms with a combined length longer than 20 nucleotides may be more sensitive and may be used when the primary objective is high sensitivity, for example, in a sample with an extremely low analyte concentration. It is important to note, that the analyte itself can be of any length from 12-40, to many thousand nucleotides.

A molecular beacon (MB) is a fluorophore- and a quencher-conjugated DNA or RNA hairpin. The probe can be customized for any fluorophore, including fluorescein amidite (FAM, 2-[3-(dimethylamino)-6-dimethyliminio-xanthen-9-yl]benzoate TAMRA, (2E)-2-[(2E,4E)-5-(2-tert-butyl-9-ethyl-6,8,8-trimethyl-pyrano[3,2-g]quinolin-1-ium-4-yl) penta-2,4-dienylidene]-1-(6-hydroxy-6-oxo-hexyl)-3,3-dimethyl-indoline-5-sulfonate Dy 750, 6-carboxy-2',4,4',5', 7,7'-hexachlorofluorescein, 4,5,6,7-Tetrachlorofluorescein TET™, sulforhodamine 101 acid chloride succinimidyl ester Texas Red-X, ALEXA Dyes, Bodipy Dyes, cyanine Dyes, Rhodamine 123 (hydrochloride), Well RED Dyes, MAX, and TEX 613; and for any quencher including BLACK HOLE QUENCHERS, IOWA BLACK QUENCHERS, and DABCYL. Molecular beacon-binding arms on each strand are typically 3-20 nucleotides long, but routine experimentation based on the molecular beacon will determine the optimum length. The length need only be long enough to bind to the molecular beacon and induce fluorescence. This means that the molecular beacon-binding arms need to be long enough to separate the fluorophore on the MB from the quencher to facilitate fluorescence when the molecular beacon is bound to the probe.

Figure 2:
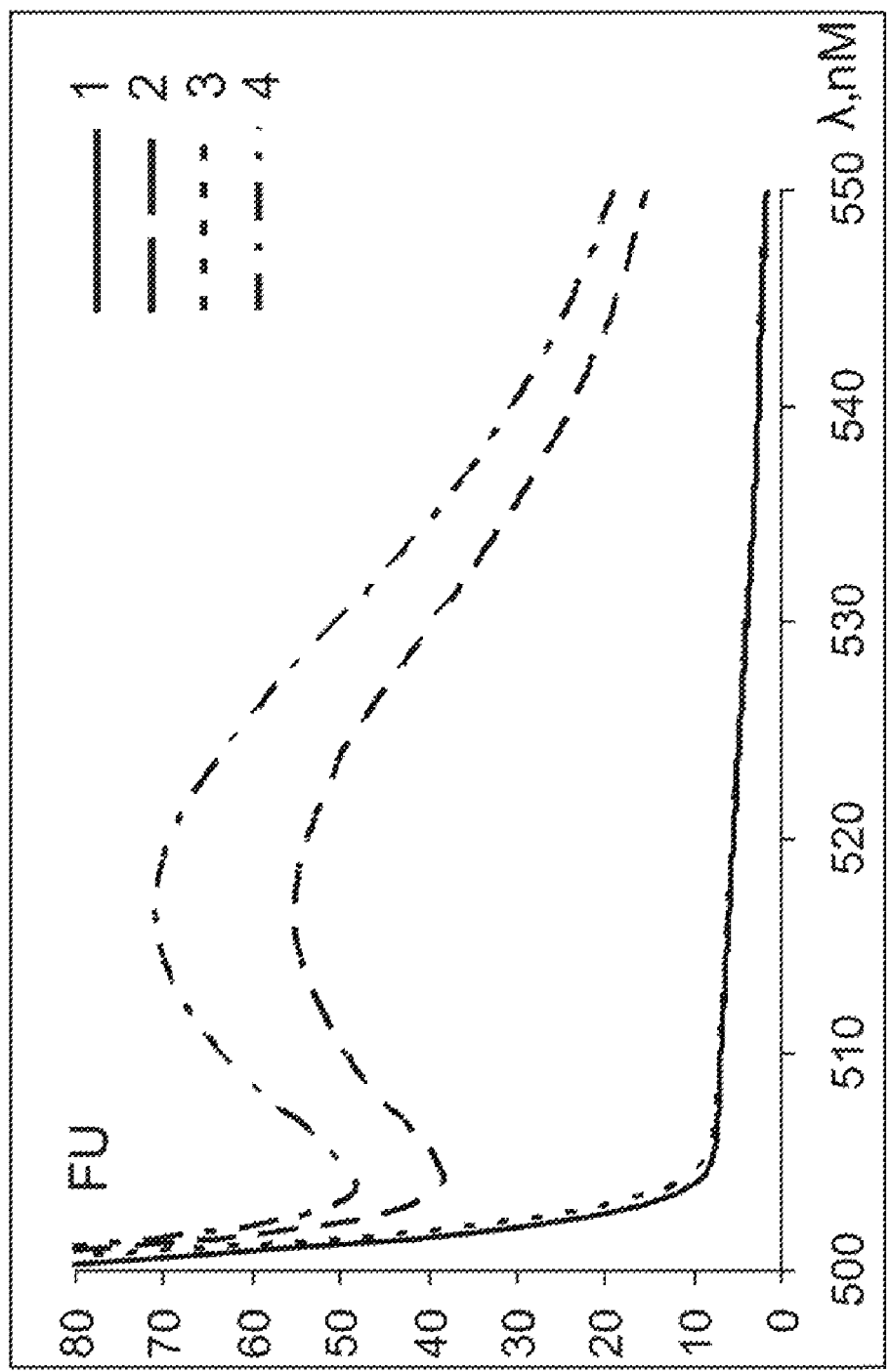
FIG. 2 BDP 10/8sl increases its fluorescence upon hybridization to A20 DNA analyte. MB1 (20 nM) together with strands A and B (500 nM each) of BDP 10/8sl were incubated in the absence (curve 1) or presence (curve 2) of 40 nM A20. Curve 3—control assay in the presence of only MB1 (20 nM); Curve 4—MB1 in the presence of 40 nM complementary oligodeoxyribonucleotide CAT AGG TCT TAA CTT C (SEQ ID NO: 19).

The analyte-binding- and molecular beacon-binding arms are separated by flexible linkers that permit the formation of two full-fledged double helixes when the analyte and molecular beacon are bound to the probe. FIG. 1A shows the BDP 10/8sl probe in which the analyte- and molecular beacon-binding arms are connected by flexible triethylene glycole linkers. Flexible linkers are also used if the binary probe is made of RNA since RNA will also form a double helix. Nucleotide linkers can also be used if they permit the formation of a double helix. In the absence of nucleic acid analyte the strands of the probe are unbound in solution, the molecular beacon is free in the form of a hairpin structure (FIG. 1A), and the fluorescent signal is low (FIG. 2, curve 1). Addition of analyte complementary to the analyte-binding arms triggers the quaternary complex formation shown in FIG. 1A (bottom) in which the analyte-binding arms bind to the analyte, thereby permitting the molecular beacon-binding arms to hybridize to the molecular beacon MB1 (SEQ ID NO. 1). When the molecular beacon binds to the probe, its hairpin structure is opened up thereby separating the fluorophore from the quencher, and the allowing fluorescent detection of the analyte hybridization event. (FIG. 2, curve 2). FIG. 2 shows that Binary DNA probe 10/8sl (that has two stem-loop structures) increases fluorescence upon hybridization to the A20 DNA analyte. MB1 (20 nM) together with strands A and B (500 nM each) of BDP 10/8sl were incubated in the absence (curve 1) or presence (curve 2) of 40 nM A20. Curve 3 is a control assay conducted in the presence of only MB1 (20 nM) without analyte. Curve 4 shows the fluorescence of MB1 in the presence of 40 nM complementary oligodeoxyribonucleotide CAT AGG TCT TAA CTT C (SEQ ID NO: 19), which hybridizes directly to MB1.

Although most molecular beacons are DNA oligonucleotides, there is no technical obstacle to making molecular beacons that are RNA or chimeras of DNA and RNA for use in the new binary RNA oligonucleotide probes.

The binary probes of the present invention are substantially destabilized by a single mismatched base pair, thereby preventing binding to the molecular beacon. The binary probes thus provide an extraordinary level of selectivity.

The new probes and analytic methods using them have the following major advantages:

1) Unprecedented high selectivity: the probes and methods permit reliable discrimination of a single base substitution at any position of a 12-20 nucleotide length or target in a DNA/RNA analyte.

2) High sensitivity: potentially a single nucleic acid molecule can be detected without PCR amplification.

3) Mild reaction conditions: the method works in buffers close to physiological conditions and at room temperature, thus being potentially applicable in living cells.

4) Relatively lower costs. The new binary probes enable specific and sensitive nucleic acid analysis and are relative cheap to make.

DNA probes have an advantage over RNA probes when the analyte is DNA because DNA-DNA duplexes are typically less stable than RNA-DNA duplexes and are therefore more sensitive to SNPs. DNA probes are cheaper also to synthesize and they are more stable to degradation in solution. In those embodiments where the probes are made of RNA oligoribonucleotides, U is substituted for T; otherwise the structures are the same. In living cells, RNA probes are preferred because RNA can be expressed in the cell as a single stranded polynucleotide. By contrast, DNA exists only as a double stranded helix inside the cell, therefore it would be functionally inactive as a probe.

It was discovered that sensitivity to a single mismatch or single nucleotide polymorphism in analytes 20 nucleotides long increased if each strand of the probe was designed to form a stem-loop hairpin structure when not bound to analyte. A stem loop structure forms by adding a nucleotide fragment of from about 3-10 nucleotides in length or up to 40 nucleotides in length (called a structure stabilization arm or SSA) to the free end of the analyte-binding arm on each strand of the probe. The added sequences in the SSA are complementary to all or part of the analyte-binding arm. When the complementary sequences in the SSA hybridize to the corresponding sequences in the analyte-binding arm, a stem-loop is formed as is shown in FIGS. 1A, B and C. The formation of stem-loops represents a conformational constraint that further increases the sensitivity of the binary DNA or RNA probes. SSA can also be added to the free end of the molecular beacon-binding arm, and can also be added to binary RNA dye-binding probes described below using any means known to one skilled in the art. When the strands of the probe are present free in solution, i.e., not hybridized to analyte, each dissociated strand of the probe is stabilized by complementary base pairing to itself via the stem loop in the analyte-binding arms (or in the molecular beacon-binding arms). This self-complementary pairing results in a "hairpin loop" structure for the individual strands, which stabilizes the oligonucleotide strands and increases sensitivity. Certain preferred embodiments of the invention are therefore directed to binary oligonucleotide probes where each strand of the probe forms a stem loop structure when the strand is not hybridized to analyte. When analytes are 16 nucleotides long or shorter, adding stem-loops to the analyte-binding arms may not be helpful.

Other embodiments are directed to variations of the binary probe structure that optimize analyte discrimination parameters. Additional changes that may increase the selectivity of the probe include shortening the analyte, for example from 20 to 12 nucleotides, or increasing the reaction temperature to 37° C., which is still within physiologic conditions that can eventually permit analyte analysis in live cells in culture or in vitro. In other embodiments the molecular beacon-binding arm on each strand of the binary probe can be varied to accommodate different reporters including molecular beacons known in or designed by those skilled in the art. Since the oligonucleotide strands of the binary probe are simple nucleotide sequences they can be made to order by various existing companies such as Integrated DNA Technologies (Coralville, Iowa, USA).

Binary RNA Dye-Binding Probes

Certain other embodiments of the present invention are directed to binary oligonucleotide probes that bind selectively to dyes, allowing the hybridization event (the binding of each probe strand to analyte) to be accompanied by an increase in fluorescence, which is easily and instantly detectable. In one embodiment the binary probe is an unmodified RNA oligonucleotide malachite green apatamer (MGA). An aptamer is a type of synthetic oligonucleotide that can bind to a particular target molecule, in this case the dye malachite green. MGA is an RNA molecule that has submicromolar affinity to malachite green (MG), a triphenylmethane dye (FIG. 4A).

A general approach for distinguishing between mismatched and fully complementary nucleic acid duplexes is to destabilize the duplexes, causing them to become sensitive to a minor imperfection such as a single base mis-pairing. The new biMGA probe/analyte hybrid is destabilized by dividing the probe into two fragments. Due to the cooperative nature of the biMGA-DNA (analyte) tripartite complex, it dissociates into three rather than two nucleic acid fragments, leading to a higher entropy gain in comparison to the conventional monolith probes. One embodiment of the invention is directed to the biMGA probe. The sequence of the first strand and second strands of the bi MGA RNA probe set forth in FIG. 4. One embodiment of the invention is directed to a truncated biMGA probe having everything but the analyte-binding arm, set forth in SEQ ID NO. 2, the second strand sequence is set forth in SEQ ID NO. 3. Without being bound by theory, we speculate that this reduction in free energy of the probe/analyte dissociated state enhances the dissociation process, especially in the presence of mismatch base-pairing.

Upon binding to analyte, MGA increases the fluorescence of the dye >2000 fold. Babendure, J. R., J. Am. Chem. Soc. 2003, 125, 9266-9270, incorporated herein by reference. To make the new probe, the MGA was separated into two anti-parallel RNA strands and analyte-binding arms were added to each strand through UU dinucleotide linkers as depicted in FIG. 4B. The inessential GAGA loop on MGA was removed to make the probe, and Stem I was shortened to three (UCC) and Stem II to four (GACC) base-pairs in order to diminish the association of the two RNA strands in solution in the absence of nucleic acid analyte. (FIGS. 4A and 4B). In the presence of DNA complementary to the analyte-binding arms, the two RNA strands of the probe cooperatively hybridize to the adjacent complementary positions of the target DNA analyte (or RNA analyte) and re-form the binary MGA probe, which allows the probe to bind the MG dye and increase fluorescence (FIG. 1C). Since each RNA strand of biMGA probe is bound to a relatively short analyte fragment, from about 6 to 20 nucleotides long, a single mismatched base pair substantially destabilizes the a hybrid, thereby destabilizing the whole complex and preventing the probe from binding the dye. Like the MB-binding binary probes, the analyte-binding arms on each strand of the dye-binding probes are from about 6-20 nucleotides long, preferably 10 nucleotides long. Dye binding probes, like MB binding probes also permit both real-time DNA detection at room temperature in a buffer simulating physiological conditions (140 mM NaCl, 5 mM KCl, 1 mM $MgCl_2$ 50 mM TrisHCl pH 7.4) and detected single nucleotide substitution in all possible positions of a 14 nucleotide DNA analyte.

In the absence of DNA analyte the biMGA probe emitted low background fluorescence (FIG. 2, curve 1) whereas addition of 2 µM A14 analyte (fully complementary to the 7 nucleic acid long analyte-binding arms on each probe) increased the fluorescence intensity about 20 times (curve 2). Fluorescence was reduced to background level in a competition assay by adding excess amounts of DNA fully complementary to the analyte (curve 3). This confirmed that the increase in fluorescence is triggered by hybridization of the analyte-binding arms to A14 analyte.

Binary dye-binding probes can be designed using any oligonucleotide strands that bind to a particular dye thereby inducing a measurable change in dye properties (for example fluorescence, phosphorescence or electronic spectra). Other aptamers that can be modified for use as a binary dye probe include a modified sulforodamine B aptamer (for the probe), and a sulforodamine dye, including but not limited to patent blue violet or patent blue VF. The Sulforodamine B aptamer sequence is:

GGAACCUCGCUUCGGCGAUGAUGGAGAG-GCGCAAGGUUAACCGCCUCA GGUUCC (SEQ ID NO: 21). Other dyes that come within the scope of the invention include triphenylmethane dyes like malachite green, including bis(N-methylindoliny), and Malichite Green IMG.

Binary probes designed to bind to analyte and to these various dyes can be designed based on the various models described herein Instead of shortening Stems 1 and 2 of the MGA aptemer as we did to make the BiMG probe (FIG. 4), we could have added structure stabilization arms to each strand that are complementary to and hybridize to an internal nucleic acid sequence in the same strand forming stem-loop structures that prevent the two halves of the probe from associating in the absence of analyte.

In the most basic embodiments, the non-naturally occurring binary oligonucleotide dye-binding probe has two antiparallel oligonucleotide strands such that the first strand has:
 a) at its 5'-terminus an analyte-binding arm, flanked by nucleotide linker or a flexible linker,
 b) the nucleotide linker or a flexible linker as described herein, that is flanked by a first stem sequence,
 c) the first stem sequence that is complementary to a corresponding first stem sequence on the second antiparallel strand, and that is flanked by a dye-binding nucleotide sequence,
 d) the dye-binding nucleotide sequence that is flanked by a second stem sequence, and
 e) at its 3'-terminus the second stem sequence that is complementary to the corresponding second stem sequence on the second antiparallel strand.

The second strand is antiparallel to the first.

In some embodiments the first stem and second stem are from 3 to 10 nucleotides long. In some embodiments the dye-binding binary probes are designed to have one or more internal stem-loop forming nucleotide sequences on each strand by adding structure stabilization arms SSA of from about 3-10 additional nucleotides to the free end of the analyte-binding arm or dye binding arm on each strand to allow formation of internal stem loop structures. When the probe is free in solution the SSA hybridize with the respective complementary sequence forming a stem loop. The size of the SSA will depend on the size of the analyte and the reporter (dye or MB), which will vary.

Figure 4:
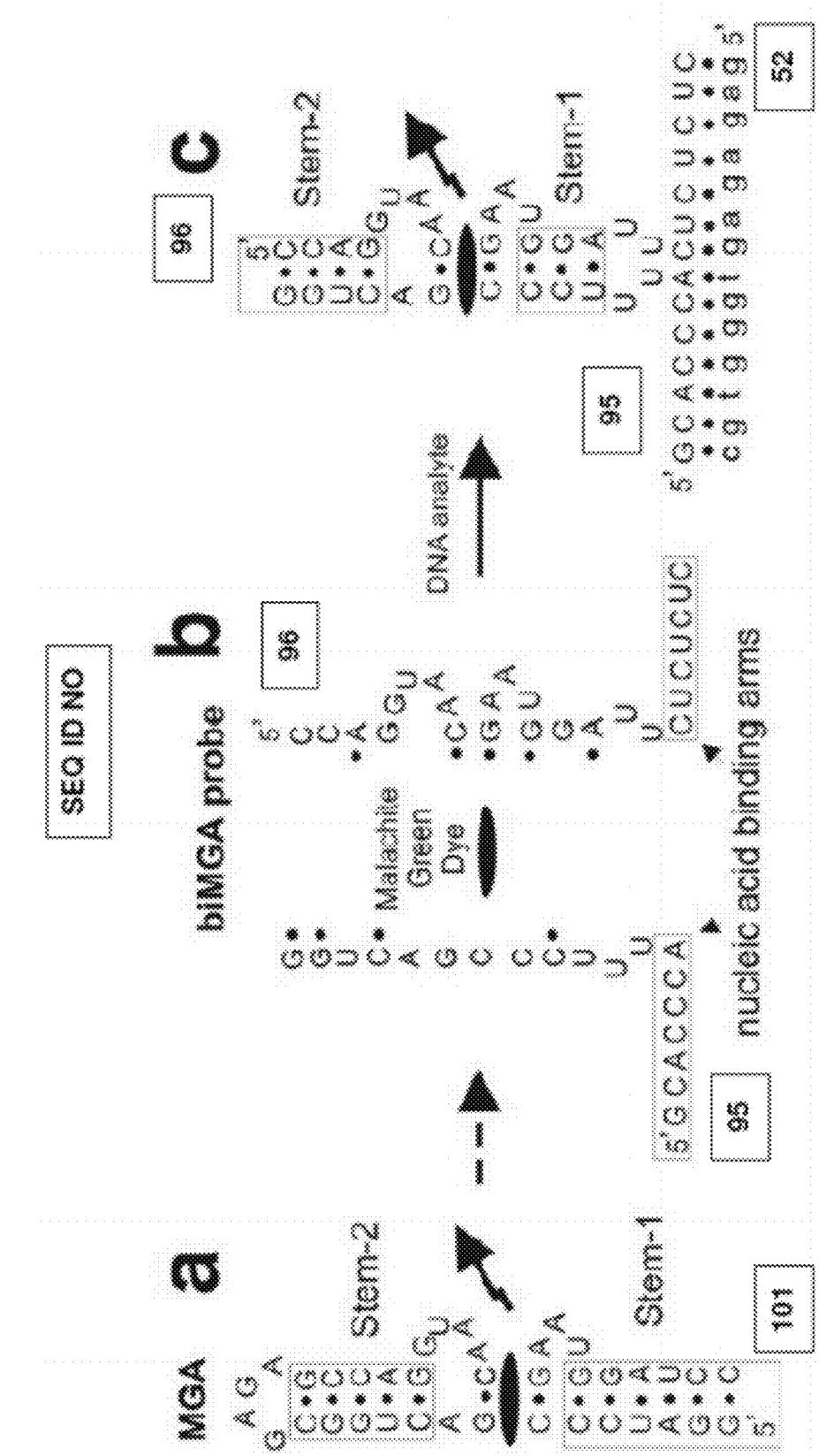
FIG. 4 (a) Structures of MGA in complex with MG. (b) The biMGA RNA probe free in solution. (c) biMGA probe bound to complementary DNA analyte. Ribonucleotides are represented in uppercase whereas deoxyribo-nucleotides are in lowercase.

A nucleotide or flexible linker joins stem 1 on each strand to the analyte-binding arms; routine experimentation will determine the optimum choice of a linker as well as its length. The linker can be a short nucleotide such as a dinucleotide uracil bridge as is shown in FIG. 4, or much longer. The linker needs to be flexible so that the probe forms a double helix when bound to analyte to separate fluorophore from quencher.

Another way of varying both the MB-binding and dye-binding probes is by using DNA or RNA analytes containing recognition domains in adjacent positions that are separated by 1, 2 or 3 nucleotides within the analyte. In this embodiment, the analyte-binding arms bind to the respective recognition domains in the analyte, but there is a 1-3 nucleotide gap in the analyte between these domains that does not have a corresponding complementary sequence in the probe to bind to. This gap may increase stability of the tertiary complex and improve catalytic efficiency which can in turn improve the speed of the reaction or increase sensitivity. Such manipulations are within routine experimentation by those skilled in the art.

Selectivity of DNA Binary Probes

The new BDPs of the present invention are substantially destabilized if there is a single mismatched base pair between the analyte-binding arm and the analyte. We discovered that BDP10/8sl reliably discriminated target analyte A20 from oligonucleotides containing single-base substitutions at any possible position (Table 1). The sequences of the 20 single-base-substituted oligodeoxyribonucleotides were designed in order to introduce one substitution in every position; the type substitution was chosen randomly. The discrimination factors (DFs) for BDP10/8sl for SNPs were significantly higher than those of a conventional MB approach indicating a higher selectivity for the BDPs. Specifically, MB2 which has the sequence set forth in SEQ ID NO. 4, an anti-A20 molecular beacon, discriminated A20 from only 15 single-base substituted oligonucleotides and did so with low DFs (Table 1). Discrimination factors were calculated as the ratio of the BDP10/8sl fluorescence intensity at 517 nM in the presence of A20 (true target) to the fluorescence intensities in the presence of each mismatched oligonucleotide after subtraction of the background fluorescence. The DFs were estimated as being higher than 10 (the signal to background ratio) for those oligonucleotides that triggered no fluorescence significantly above the background. The mismatched positions are underlined. The data are the average of four independent measurements. Blank cells=DF=1.

Surprisingly, the presence of four substituted oligonucleotides did not trigger BDP 10/8sl fluorescence significantly above the background (Table 1). The probe was insensitive to the presence of A20-1, A20-4, A20-8, and A20-17 at the concentration used. The fluorescence of the probe in this series of experiments was magnesium dependent with a maximum signal to background ratio at 15-30 mM $Mg^{2+}$ (data not shown). All experiments presented in this series were done using 25 mM $MgCl_2$ 10 mM Tris HCl pH 7.4 buffer. Without being limited by theory, it may be that the high $Mg^{2+}$ concentration stabilizes the four way junction-like structure having the two negatively charged double helixes close to each other.

TABLE 1

Discrimination factors (DFs) for oligodeoxyribonucleotides differing from A20 by a single nucleotide

| Oligodeoxyribonucleotides Names | Sequences (SEQ ID NO) | BDP10/8sl | MB2* | BDP8/8 | BDP10/8 |
|---|---|---|---|---|---|
| A20 | ATGGAGAGAG TGGGTGCGAG (22) | 1 | 1 | 1 | 1 |
| A20-1 | TTGGAGAGAG TGGGTGCGAG (23) | >10.0 | 2.1 ± 0.6 | | >10 |
| A20-2 | AGGGAGAGAG TGGGTGCGAG (24) | 1.8 ± 0.1 | 0.9 ± 0.2 | | 1.0 ± 0.1 |
| A20-3 | ATAGAGAGAG TGGGTGCGAG (25) | 3.8 ± 1.4 | 1.1 ± 0.1 | 1.2 ± 0.1 | 1.3 ± 0.1 |
| A20-4 | ATGTAGAGAG TGGGTGCGAG (20) | >10.0 | 2.1 ± 0.3 | >10 | >10 |
| A20-5 | ATGGCGAGAG TGGGTGCGAG (26) | 9.2 ± 1.9 | 2.3 ± 0.6 | >10 | 5.8 ± 1.2 |
| A20-6 | ATGGATAGAG TGGGTGCGAG (27) | 9.2 ± 4.1 | 1.2 ± 0.1 | >10 | 3.5 ± 0.8 |
| A20-7 | ATGGAGGGAG TGGGTGCGAG (28) | 6.9 ± 1.7 | 1.2 ± 0.2 | 4.0 ± 0.9 | 1.2 ± 0.2 |
| A20-8 | ATGGAGAAAG TGGGTGCGAG (29) | >10.0 | 1.6 ± 0.1 | >10 | >10 |
| A20-9 | ATGGAGAGCG TGGGTGCGAG (30) | 11.5 ± 2.5 | 1.6 ± 0.1 | >10 | 5.0 ± 0.9 |
| A20-10 | ATGGAGAGAT TGGGTGCGAG | >10.0 | 1.1 ± 0.1 | >10 | 12.6 ± 3.8 |

TABLE 1-continued

Discrimination factors (DFs) for oligodeoxyribonucleotides differing from A20 by a single nucleotide Oligodeoxyribonucleotides

| Names | Sequences (SEQ ID NO) | BDP10/ 8sl | MB2* | BDP8/8 | BDP10/8 |
|---|---|---|---|---|---|
| A20-11 | ATGGAGAGAG GGGGTGCGAG (31) | 3.0 ± 0.5 | 1.3 ± 0.2 | 2.1 ± 0.3 | 2.2 ± 0.1 |
| A20-12 | ATGGAGAGAG TAGGTGCGAG (32) | 5.5 ± 2.5 | 1.1 ± 0.1 | 6.3 ± 1.9 | 1.9 ± 0.2 |
| A20-13 | ATGGAGAGAG TGTGTGCGAG (33) | 3.5 ± 0.8 | 1.3 ± 0.1 | 4.6 ± 1.4 | 1.6 ± 0.1 |
| A20-14 | ATGGAGAGAG TGGTTGCGAG (34) | 3.5 ± 1.0 | 1.2 ± 0.1 | 5.1 ± 1.4 | 1.8 ± 0.1 |
| A20-15 | ATGGAGAGAG TGGGAGCGAG (35) | 3.4 ± 0.6 | 1.3 ± 0.2 | 4.1 ± 1.3 | 1.6 ± 0.1 |
| A20-16 | ATGGAGAGAG TGGGTTCGAG (36) | 3.2 ± 0.8 | 1.2 ± 0.1 | 5.0 ± 1.4 | 1.8 ± 0.2 |
| A20-17 | ATGGAGAGAG TGGGTGTGAG (37) | >10 | 2.5 ± 0.6 | 10.6 ± 2.2 | 8.7 ± 1.4 |
| A20-18 | ATGGAGAGAG TGGGTGCCAG (38) | 5.5 ± 1.3 | 1.3 ± 1.2 | 2.4 ± 0.4 | 2.6 ± 0.3 |
| A20-19 | ATGGAGAGAG TGGGTGCGGG (39) | 2.2 ± 0.5 | 1.2 ± 0.1 | | 2.0 ± 0.3 |
| A20-20 | ATGGAGAGAG TGGGTGCGAA (40) | 1.6 ± 0.3 | 1.1 ± 0.1 | | 1.7 ± 0.2 |

Figure 3:
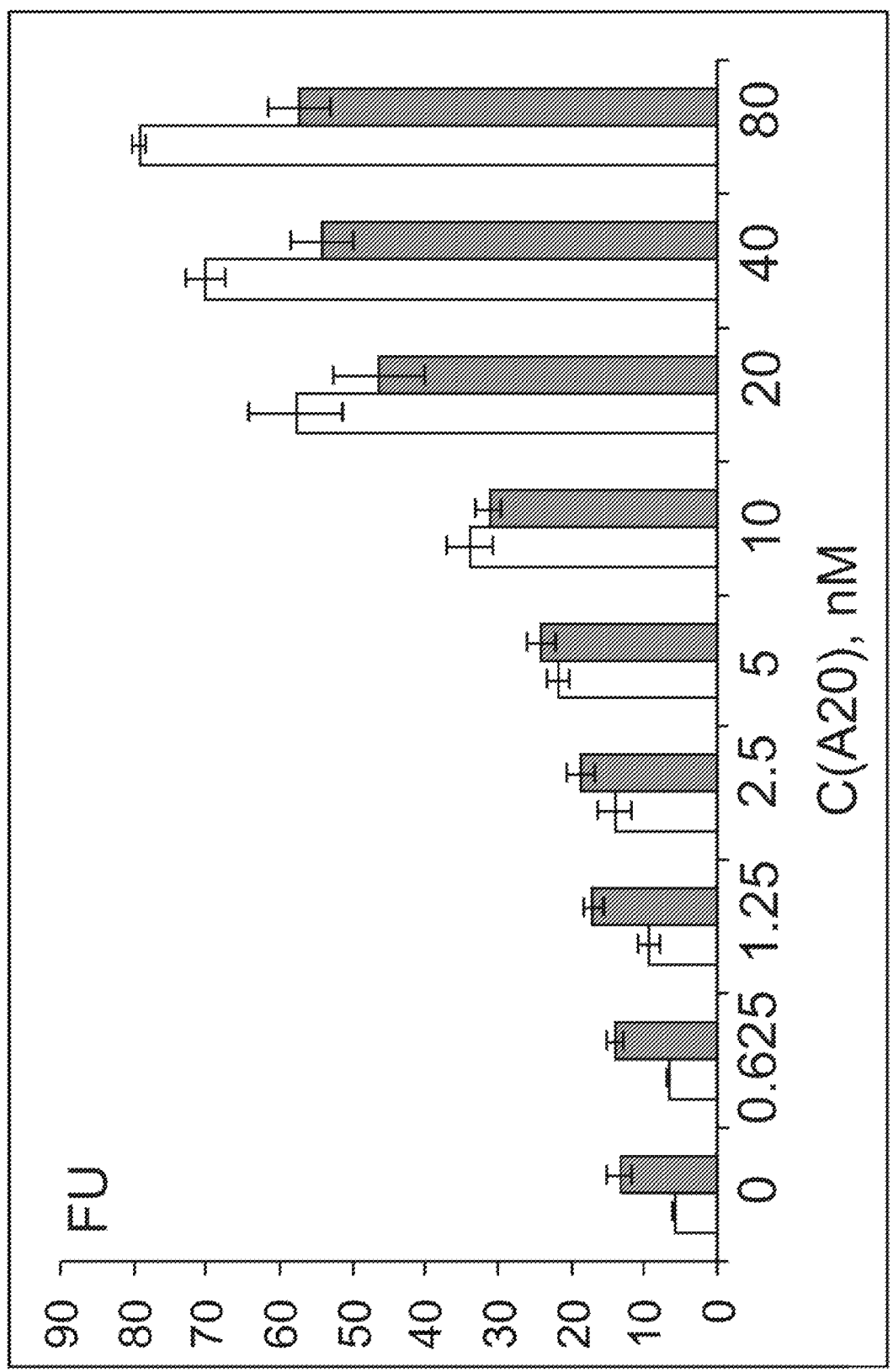
FIG. 3 The dependence of BDP10/8 sl fluorescence intensity on A20 concentration in the absence (white bars) or presence (gray bars) of 500 nM A20-4 (ATG TAG AGA GTG GGT GCG AG (SEQ ID NO: 20)).

Another experiment was designed to test the ability of BDP10/8sl to detect true A20 analyte in a solution containing an excess of analyte with a single base substitution at position 4: A20-4. FIG. 3 shows the dependence of BDP10/8 sl fluorescence intensity on true analyte A20 concentration in the absence (white bars) or presence (gray bars) of 500 nM A20-4 (ATG TAG AGA GTG GGT GCG AG (SEQ ID NO: 20)). The presence of excess A20-4 (500 nM) increased background fluorescence by only about 2 times. By contrast, background fluorescence was significantly increased when 2.5 nM the true A20 target was added, even though the analyte concentration was only 0.5% of the concentration of A20-4. This extremely high specificity of the probe means that the new binary DNA probes can be used in minority point mutation analysis directly after conventional PCR, thus avoiding additional work-intensive enzyme-mediated steps used by more conventional approaches.

Table 1 also gives the results of selectivity experiments using BDP variants that do not have a stem loop (sl) structural constraints: binary DNA probe 8/8 and 10/8 (FIG. 1B). Both probes demonstrated excellent selectivity in recognizing a 20 nucleotide DNA fragment (Table 1). However, when the analyte-binding arms were elongated to 10 nucleotides the selectivity for the 16 nucleotide DNA fragment was notably decreased because there was no stem loop structure (compare discrimination factors in Table 1). BDP with SSA are a preferred embodiment.

Binary DNA Probes Detect *Francisella tularensis* 16S rRNA Sequence

Recently an application of the MB approach was reported to discriminate a unique region of the 16S rRNA of the bacterium *Francisella tularensis* (a fragment designated CS11) from mutant 16sRNA. Ramachandran, A. et al., *Biosens. Bioelectron,* 2004, 19, 727-736. *F. tularensis* is a potential biological weapon and a highly infectious bacterium. The sequence for CS11 is shown in Table 2. The molecular beacons alone hardly discriminated single base substituted CS111 and double base-substituted forms CS120 and CS122 even using buffers optimized for using MBs. Thus the MB approach alone did not allow discrimination of these oligonucleotides.

We designed a new BDP with customized analyte-binding arms called "BDP 10/8 *F. tul*" to recognize the 16sRNA represented by oligodeoxyribonucleotide CS11. An embodiment of the invention is directed to the BDP10/8sl *Francisella tularensis* probe shown in FIG. 1C, which has the same MB1 binding arms as BDP10/8sl. The sequence of the strand A (the first strand) analyte binding arm is set forth in SEQ ID NO. 17; strand B is set forth in SEQ ID NO. 18. Certain embodiments are directed to the analyte binding arms, and a truncated probe having only reporter binding arms with or without a linker. The customized analyte-binding arms are fully complementary to the true CS11 analyte with each arm having 10 complementary nucleotides. We also added customized molecular beacon stabilization arms (SSA) that are complementary to a portion of the analyte-binding arm in order to introduce a stem loop structure into the probe when it is unbound and in solution. The stem loops have four-nucleotides (strand A), or five-nucleotides (strand B). The new probe BDP10/8sl *F. tul* reliably discriminated all ten test oligonucleotides tested from the true CS11 analyte (Table 2). It should be emphasized that four out of 10 single base-substituted oligonucleotides including CS120 and CS122 triggered no fluorescence substantially higher than the background. This result demonstrates a remarkably improved selectivity compared to using molecular beacons alone. The design of the customized BDP 10/8 *F. tul* was straightforward and easy. The sequence of the analyte-binding arms and adding the SSA was the only change made to adjust the parent BDP to the new analyte, while the same MB was used as a fluorescent reporter. Taking into account the relative expense of MB probes, the BDP may substantially reduce the cost of multi-target assays in comparison to conventional MB approach.

TABLE 2

Discrimination factors for BDP10/8 Ful.

| Oligonucleotide Name | Sequence (SEQ ID NO) | DF |
|---|---|---|
| CS11 | GCCTTGGGGG AGGACGTTAC (42) (true target) | 1 |
| CS111 | GCTTTGGGGG AGGACGTTAC (43) | 1.6 ± 0.2 |
| CS112 | ACCTTGGGGG AGGACGTTAC (44) | 1.6 ± 0.1 |
| CS113 | GTCTTGGGGG AGGACGTTAC (45) | >5.0 |
| CS114 | GCCTTGGGGA AGGACGTTAC (46) | 10.1 ± 1.8 |
| CS115 | GCCTTGGGGG AGGACGTTAT (47) | 7.1 ± 0.7 |
| CS116 | GCCTTGGGGG AG GAT GTTAC (48) | 2.2 ± 0.3 |
| CS117 | GCCTTGGGGG AGGACGTCAC (49) | >5.0 |
| CS120 | GCCTTGGGGA GGGACGTTAC (50) | >5.0 |
| CS122 | GTCTTGGGGA AGGACGTTAC (51) | >5.0 |

DFs in Table 2 were calculated as in Table 1. The data are the average of four independent experiments. The DFs were estimated as being higher than 5 (signal to background ratio) for those oligonucleotides that triggered no fluorescence significantly above the background. To optimize the fluorescent read-out of an assay, the concentrations of each component of the mixture can be optimized to achieve a fast and rigorous fluorescent response only after addition of DNA or RNA analyte.

Selectivity of the Binary RNA Dye-Binding Probe

We conducted experiments in which the fluorescence intensity of the biMGA probe in the presence of fully-matched target A14 analyte was compared to the fluorescence intensities in the presence of oligonucleotides containing all possible single nucleotide substitutions (Table 3). The sequence of analyte target A14 is (5'-$g_1a_2g_3a_4g_5a_6g_7t_8g_9g_{10}g_{11}t_{12}g_{13}c_{14}$ (SEQ ID NO: 52)). Discrimination factors were calculated as a ratio of the fluorescence intensity of biMGA in the presence of A14 to fluorescence in the presence of mismatched oligonucleotides (after subtraction of background fluorescence). Fully complementary analyte binding should give a DF of 1. The discrimination factors shown in Table 4 were estimated as being higher than 20 for those oligonucleotides having single nucleotide polymorphisms (SNPs) that failed to trigger an increase in fluorescence above background. DFs higher than 20 indicate a very high level of selectivity of the probe. Blank cells had a DF=1. The probe reliably discriminated SNP mismatches at all positions of the A14 analyte, except the substitution of T by A at $8^{th}$ position. The best discrimination was observed against mismatches located at internal positions of the two RNA/DNA hybrids. For 25 out of 42 oligonucleotides the fluorescence intensity did not exceed the background. Particularly remarkable demonstrations of the specificity of the probe are a good discrimination (DF=4.5±0.9) of the T-G from C-G base pair at the 3' terminal position of the DNA analyte (Table 4, last row, $5^{th}$ column) and a discrimination A-U from G-U (DF>20) at $4^{th}$ position of A14 (Table 4, row 4, column 2). The concentrations of all oligodeoxyribonucleotides were 2 µM. The values are averages of four independent experiments. Cells that are blank indicate full complementary and a DF of 1.

TABLE 3

Structures of single-base substituted A14 oligodeoxyribonucleotides.

| Substituted position | Substituted with | | | |
|---|---|---|---|---|
| | a | c | g | t |
| 1 | aagagag tgggtgc (SEQ ID NO: 53) | cagagag tgggtgc (SEQ ID NO: 54) | — | tagagag tgggtgc (SEQ ID NO: 55) |
| 2 | — | gcgagag tgggtgc (SEQ ID NO: 56) | gggagag tgggtgc (SEQ ID NO: 57) | gtgagag tgggtgc (SEQ ID NO: 58) |
| 3 | gaaagag tgggtgc (SEQ ID NO: 59) | gacagag tgggtgc (SEQ ID NO: 60) | — | gatagag tgggtgc (SEQ ID NO: 61) |
| 4 | — | gagcgag tgggtgc (SEQ ID NO: 62) | gagggag tgggtgc (SEQ ID NO: 63) | gagtgag tgggtgc (SEQ ID NO: 64) |
| 5 | gagaaag tgggtgc (SEQ ID NO: 65) | gagacag tgggtgc (SEQ ID NO: 66) | — | gagatag tgggtgc (SEQ ID NO: 67) |
| 6 | — | gagagcg tgggtgc (SEQ ID NO: 68) | gagaggg tgggtgc (SEQ ID NO: 69) | gagagtg tgggtgc (SEQ ID NO: 70) |
| 7 | gagagaa tgggtgc (SEQ ID NO: 71) | gagagac tgggtgc (SEQ ID NO: 72) | — | gagagat tgggtgc (SEQ ID NO: 73) |

TABLE 3-continued

Structures of single-base substituted A14 oligodeoxyribonucleotides.

| Substituted position | Substituted with | | | |
|---|---|---|---|---|
| | a | c | g | t |
| 8 | gagagag agggtgc (SEQ ID NO: 74) | gagagag cgggtgc (SEQ ID NO: 75) | gagagag ggggtgc (SEQ ID NO: 76) | — |
| 9 | gagagag taggtgc (SEQ ID NO: 77) | gagagag tcggtgc (SEQ ID NO: 78) | — | gagagag ttggtgc (SEQ ID NO: 79) |
| 10 | gagagag tgagtgc (SEQ ID NO: 80) | gagagag tgcgtgc (SEQ ID NO: 81) | — | gagagag tgtgtgc (SEQ ID NO: 82) |
| 11 | gagagag tggatgc (SEQ ID NO: 83) | gagagag tggctgc (SEQ ID NO: 84) | — | gagagag tggttgc (SEQ ID NO: 85) |
| 12 | gagagag tggagc (SEQ ID NO: 86) | gagagag tgggcgc (SEQ ID NO: 87) | gagagag tgggggc (SEQ ID NO: 88) | — |
| 13 | gagagag tgggtac (SEQ ID NO: 89) | gagagag tgggtcc (SEQ ID NO: 90) | — | gagagag tgggttc (SEQ ID NO: 91) |
| 14 | gagagag tgggtga (SEQ ID NO: 92) | — | gagagag tgggtgg (SEQ ID NO: 93) | gagagag tgggtgt (SEQ ID NO: 94) |

TABLE 4

Discrimination Factors For Oligodeoxyribonucleotides Differing From A14 by a Single Nucleotide

| Substituted position | Substituted with | | | |
|---|---|---|---|---|
| | a | c | g | t |
| 1 | 2.8 ± 0.4 | 2.4 ± 0.5 | — | 2.0 ± 0.2 |
| 2 | — | 13.7 ± 1.2 | >20 | 5.5 ± 1.8 |
| 3 | >20 | >20 | — | >20 |
| 4 | — | >20 | >20 | >20 |
| 5 | >20 | >20 | — | >20 |
| 6 | — | 15.3 ± 4.4 | >20 | 5.5 ± 1.7 |
| 7 | 8.4 ± 2.0 | 6.0 ± 2.0 | — | 6.3 ± 2.2 |
| 8 | 0.7 ± 0.2 | 2.1 ± 0.6 | 2.0 ± 0.4 | — |
| 9 | >20 | >20 | — | >20 |
| 10 | >20 | >20 | — | >20 |
| 11 | >20 | >20 | — | >20 |
| 12 | >20 | >20 | 15.5 ± 3.6 | — |
| 13 | >20 | >20 | — | >20 |
| 14 | 7.0 ± 1.2 | — | 7.0 ± 1.8 | 4.5 ± 0.9 |

Figure 6:
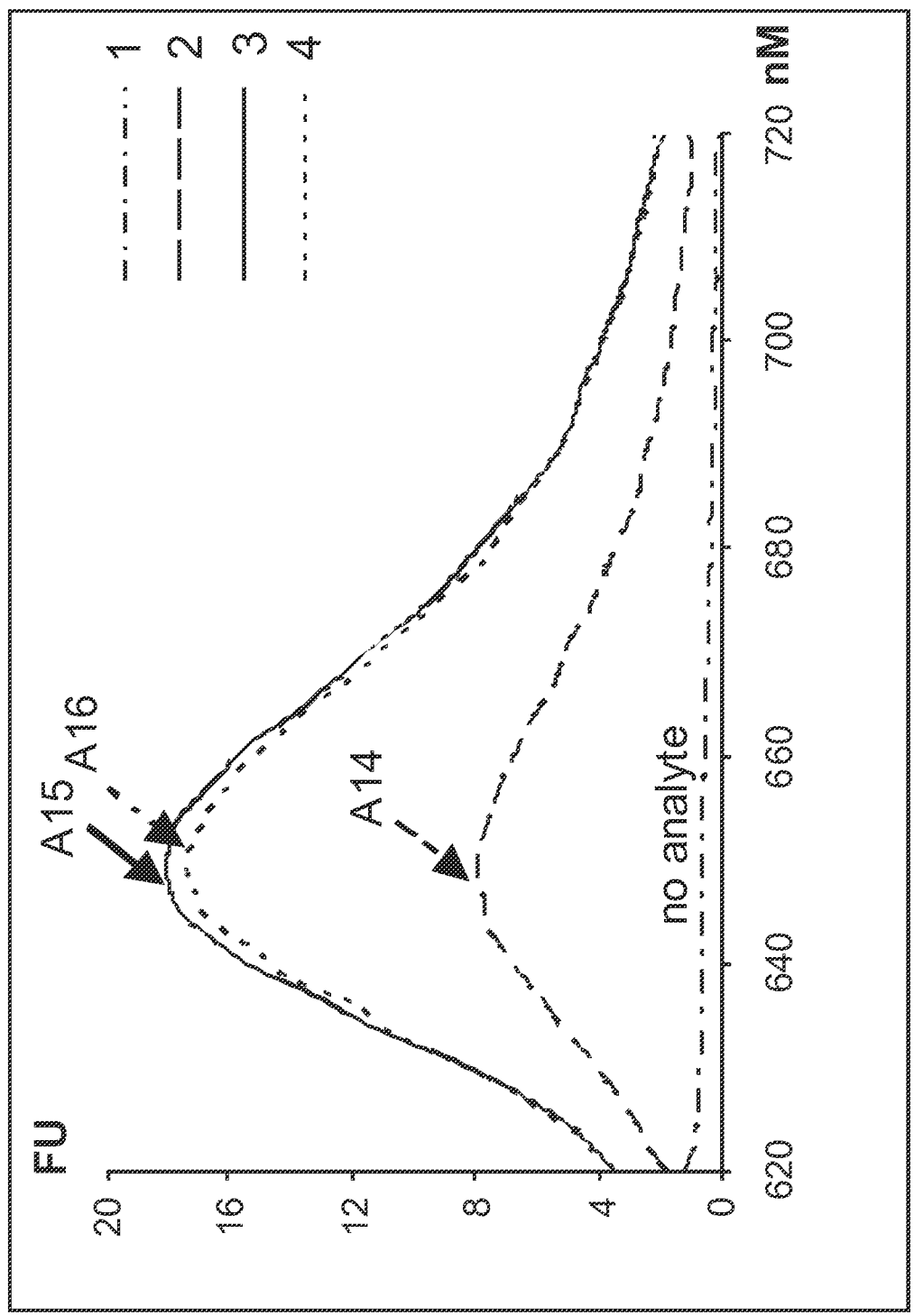
FIG. 6 Binary Malachite Green Aptamer probe fluorescence spectra in the presence of 2 µM A 14 (curve 2), A 15 (curve 3) or A 16 (curve 4). Curve 1 in the absence of DNA analyte.
Figure 7:
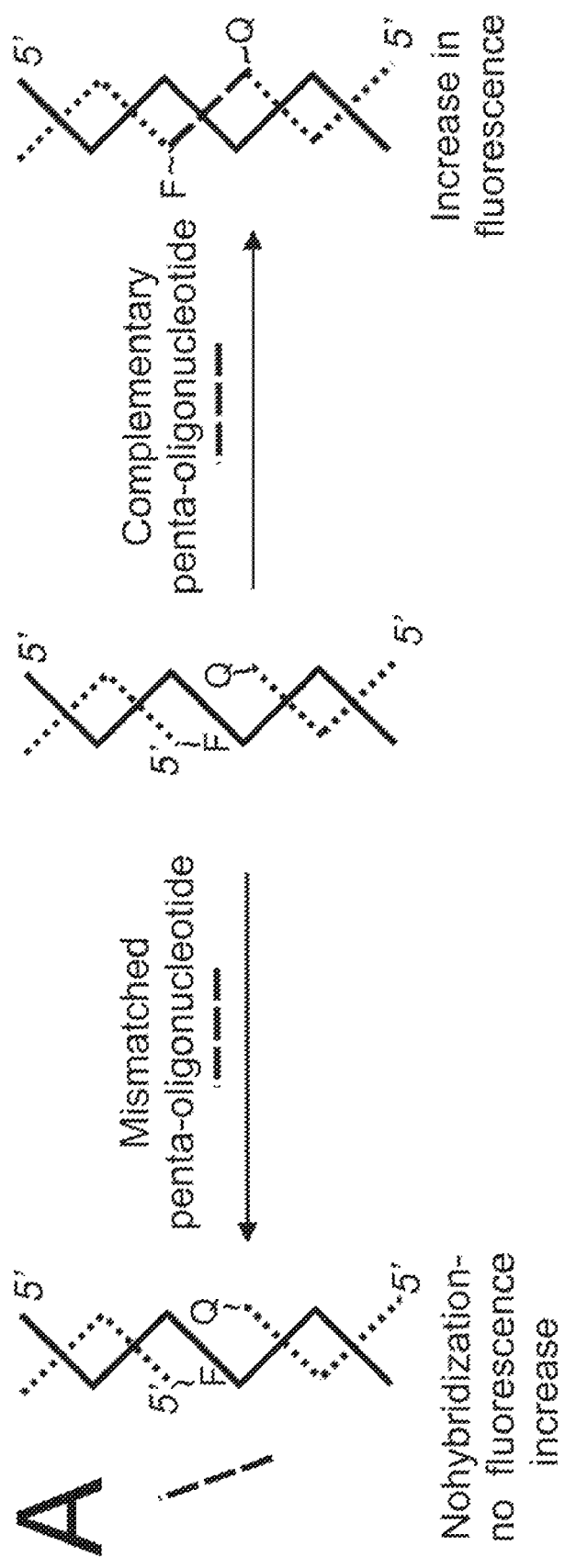
FIG. 7 Principal scheme of the fluorescent oligonucleotide tandem for SNP analysis.
Figure 8:
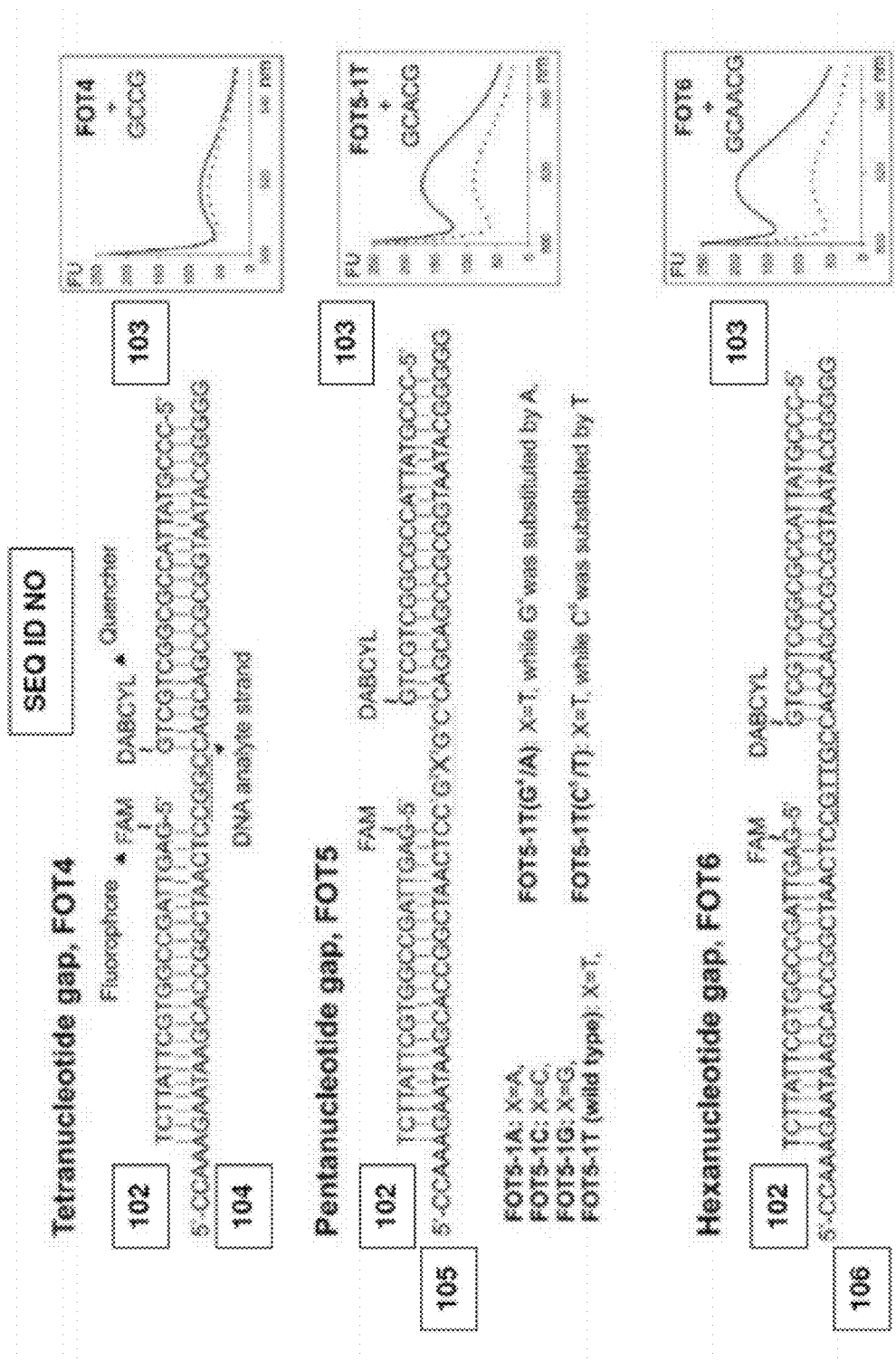
FIG. 8 Fluorescent oligonucleotide tandems. A. Primary and secondary structure; B. Fluorescent response of the tetra-, penta-, and hexanucleotide gaps to the presence of gap-filling oligonucleotides.
Figure 9:
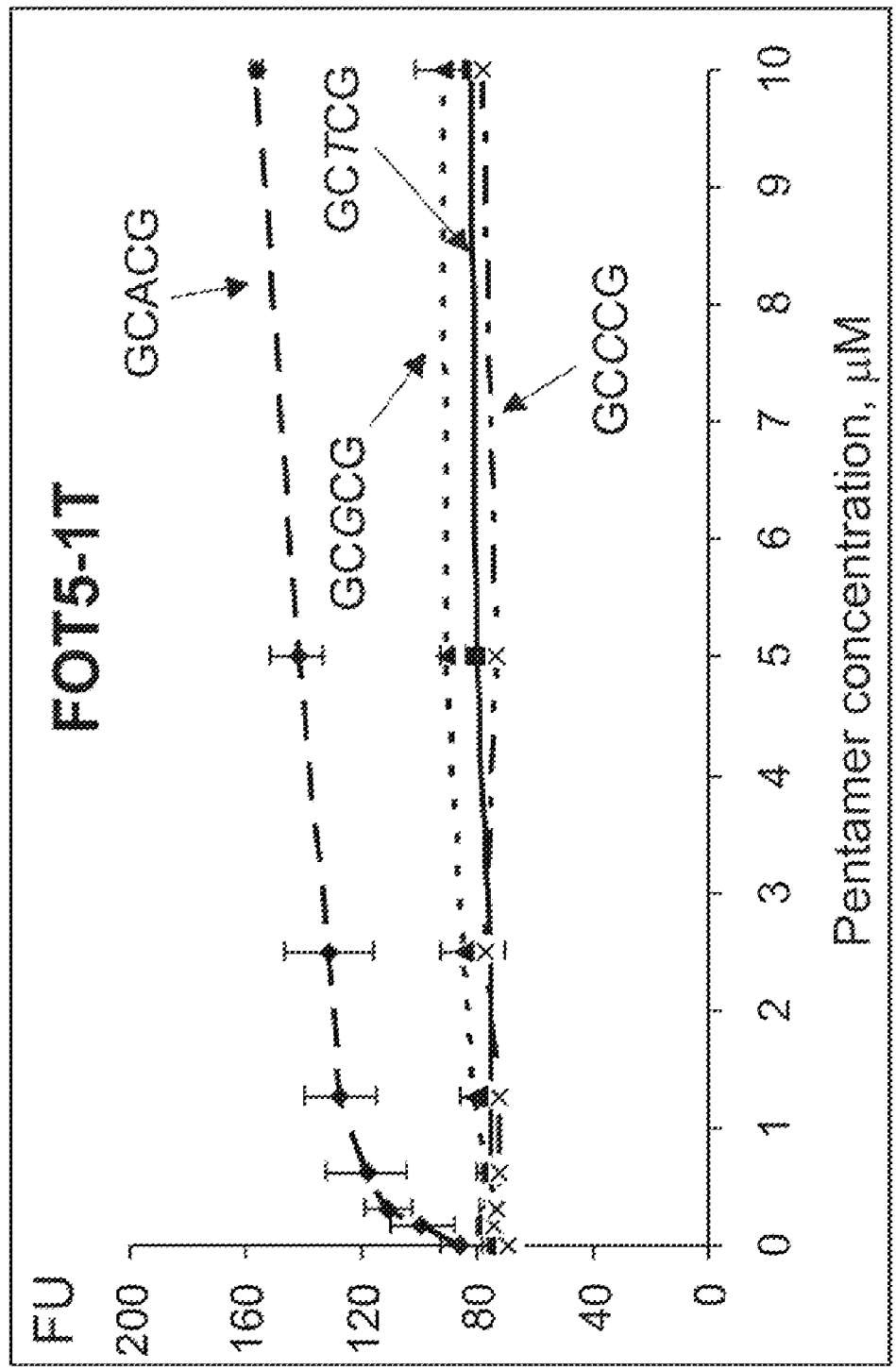
FIG. 9 FOT5-1T generates higher fluorescence in the presence of the fully complementary pentanucleotide GCACG, than with mismatched pentanucleotides. (FOT=Fluorescent oligonucleotide tandem)
Figure 10:
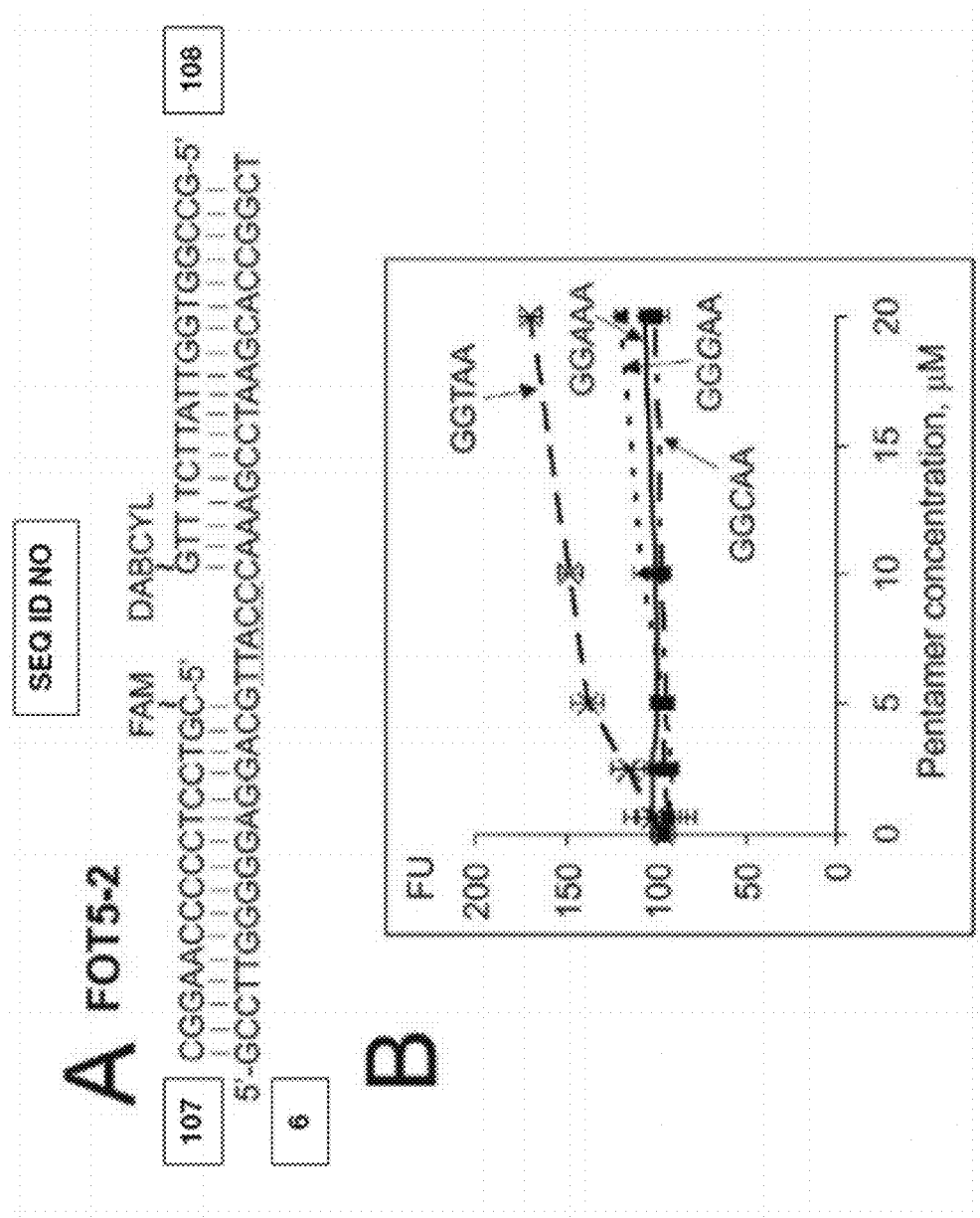
FIG. 10 A. Primary and secondary structure of FOT5-2. B. Flourescence of FOT tandems depends on the concentrations of gap-filling pentanuceotides. The values are averages of three independent measurements.
Figure 11:
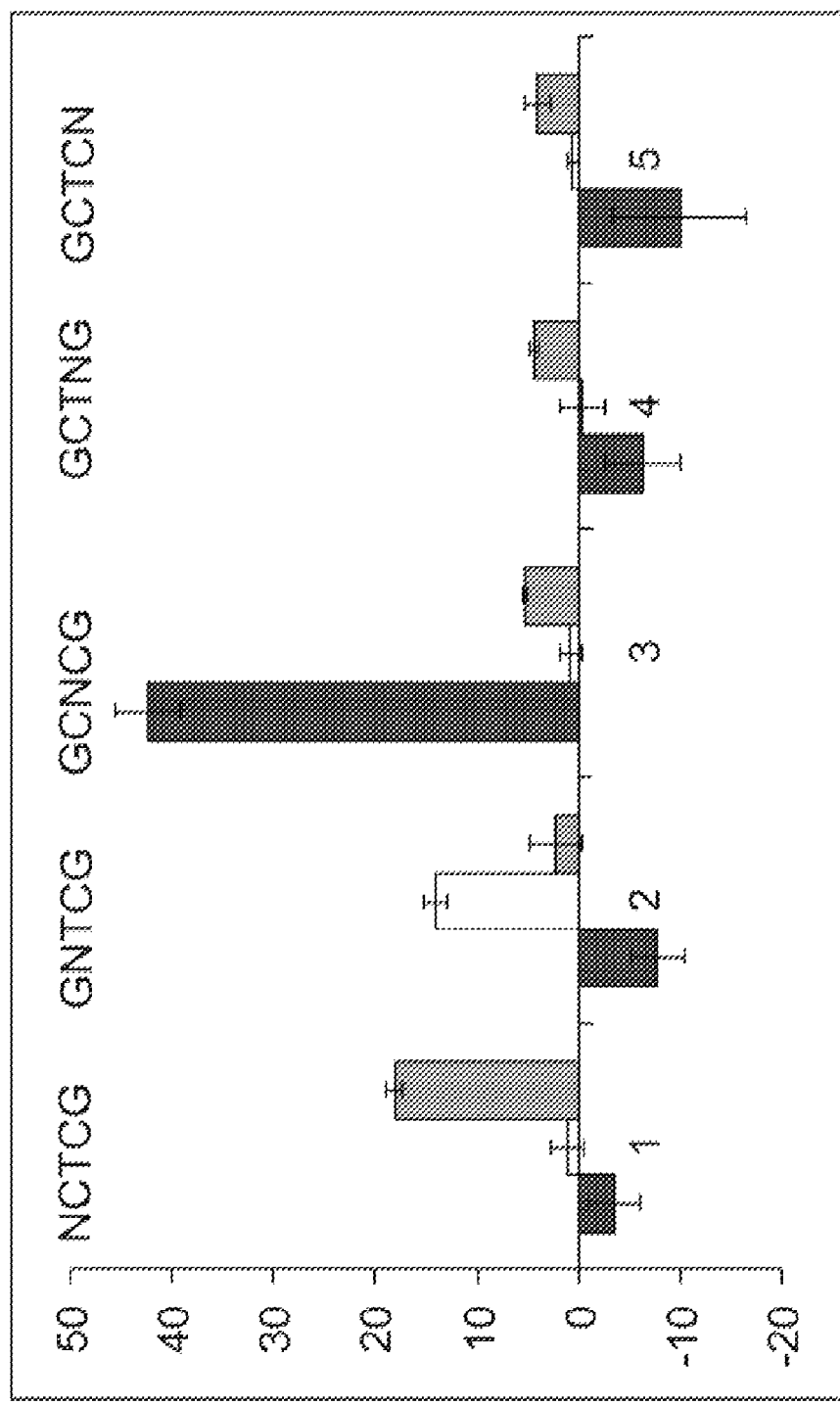
FIG. 11 FOT5-1C (dark bars, FOT5-1T(G4/A) (white bars and FOT-1T(C5/t) (gray bars) in the presence of pentanucleotide libraries. The values are averages of three independent measurements.
Figure 12:
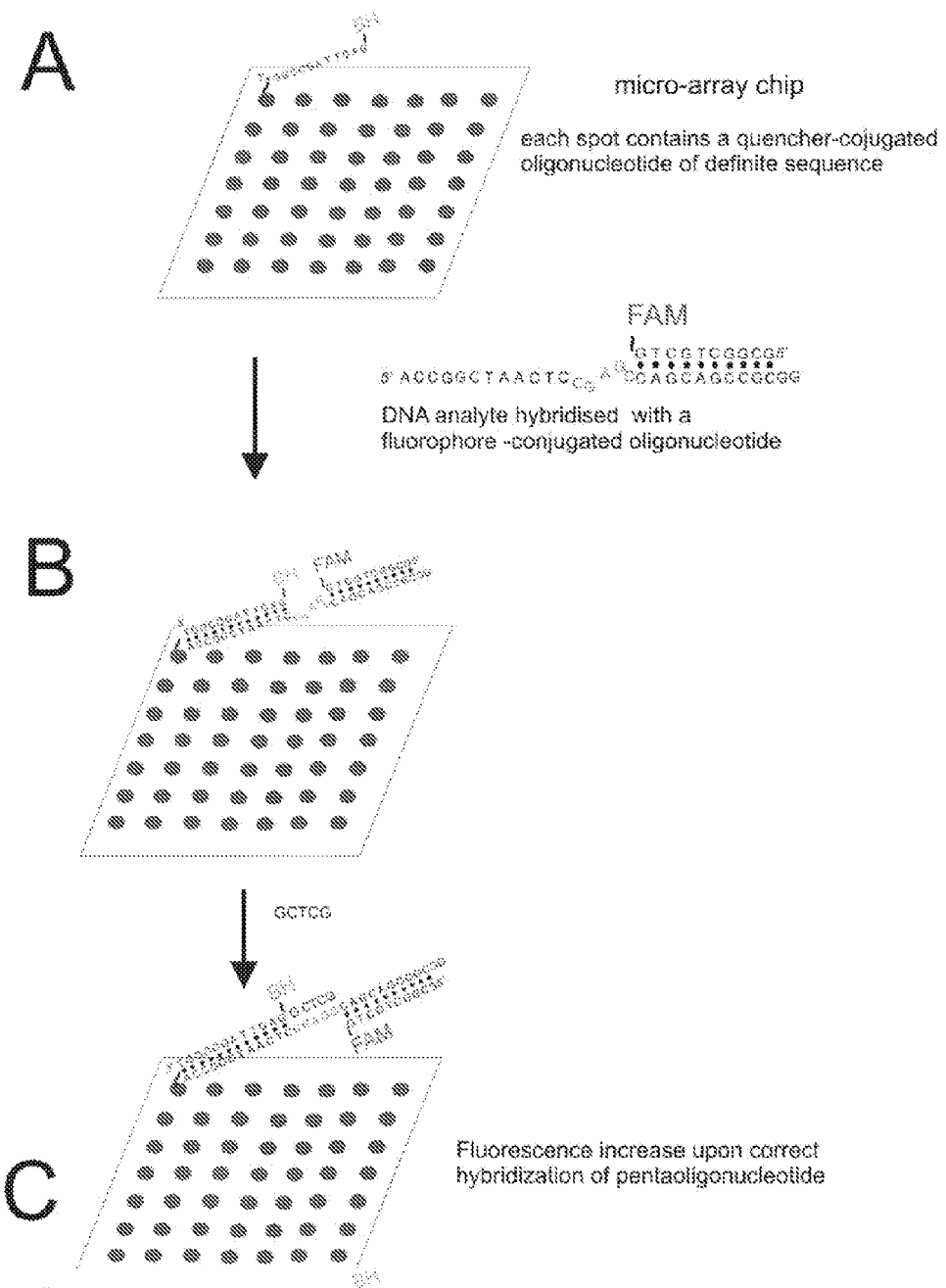
FIG. 12 A microarray scheme for using FOTs to identify target analytes.

Interestingly, an oligonucleotide containing T to A substitution at position 8 triggered higher fluorescence then A14 (DF=0.7±0.2). This may be due to base pair formation between the A8 of the deoxyoligonucleotide and one of the Us of the UU bridges. It is possible that such a complex favors RNA strands to form stable MG binding site. The substitution of UU bridges with other linkers will allow an improvement in discrimination against T-A substitution at this position. Routine experimentation with various linkers, including the flexible linkers described above, will identify the best probe design for the particular analyte. We also discovered that separating nucleotide recognition sites by one or two nucleotides causes the ensuing fluorescence signal of the complex to increase even higher than the signal for the A14 DNA analyte (FIG. 6). This result indicates that biMGA probes can be designed for selective recognition of not only adjacent fragments of nucleic acids but also of fragments separated by a few nucleotides.

The probe reliably discriminated 41 out of 42 possible single nucleotide substitutions in 14-mer DNA analyte with extremely high discrimination factors (>20) for more than half of the possible substitutions. These high discrimination abilities biMGA probe demonstrates at room temperature in a buffer simulating physiological conditions. The biMGA consists entirely of unmodified RNA, it does not have any dye or other label attached and therefore it can be expressed in living cells as a gene product. All these factors taken together make biMGA a promising instrument for highly selective fluorescent monitoring of nucleic acids in cell culture and in vivo.

Hybridization Assays and Kits for Making and Using the Binary Fluorescent Probes Certain embodiments are also directed to a binary oligonucleotide probe hybridization assay to detect RNA or DNA analyte in a sample containing a heterogeneous mixture of nucleic acids including at least one single stranded analyte molecule that has a known nucleotide sequence. The assay has the following steps:
   a) providing a first binary oligonucleotide probe described above, wherein the nucleotides in the analyte-binding arms of the first probe are complementary to the known nucleotide sequence in the first analyte,
   b) providing a first molecular beacon that fluoresces at a first wavelength and that selectively hybridizes to the molecular beacon-binding arms on the first probe,
   c) creating a mixture comprising the first binary probe and the first molecular beacon,
   d) determining a first background level of fluorescence of the first molecular beacon for the mixture of step c,
   e) adding the sample to the mixture of step c,
   f) maintaining said mixture of step e for a sufficient period of time and under predetermined reaction conditions to allow the analyte to hybridize to the analyte-binding arms on the first probe, and for the first molecular beacon to hybridize to the molecular beacon-binding arms on the first probe, then
   g) determining that the analyte is present in the sample if the level of fluorescence of the first molecular beacon increases above the first background level.

More than one analyte can be detected in a single assay using two or more different binary probes that each have 1-customized analyte-binding arms that are complementary to and hybridize with a specific unique analyte having a known nucleotide sequence, and 2-customized molecular beacon-binding arms that recognize and bind to a specific, unique MB that can be distinguished from other MB. Such customization procedures are routine in the art.

Certain embodiments of the invention are directed to truncated forms of the binary probe ("the truncated probe"). In its simplest form each truncated BDP probe strand has only the molecular beacon-binding arms and flexible linkers, with optional structure stabilization arms internally complementary to a portion of the respective molecular beacon-binding arm. The user can customize the analyte-binding arms to suit the target. Certain embodiments are directed to a diagnostic fluorescent binary oligonucleotide probe hybridization assay kit to detect a known RNA or DNA analyte in a sample containing a heterogeneous mixture of nucleic acids, the kit comprising 1. a binary oligonucleotide DNA or RNA probe as described herein that is complementary to and selectively hybridizes with the known DNA or RNA analyte, and 2. a molecular beacon that binds to the probe when the probe is hybridized to the known analyte.

Alternatively diagnostic kits would have one or more molecular beacons, and one or more complete binary probes with predetermined analyte-binding arms that bind to a specific analyte that indicates the presence (or absence) of a virus, bacterial endotoxin, cancer antigen or other disease marker, indicating the presence of a condition such as a disease including cancer. In one embodiment, a multiplex format is prepared having different binary probes that recognize different reporters (for example fluorogenic MB) for each different analyte. In an embodiment the fluorogenic molecular beacons will be labeled by differently colored fluorophores, enabling assays to be carried out that simultaneously detect different targets in the same reaction. A large variety of reporters including fluorophores can be used (such as FAM, TET, TAMRA and others known in the art), and quenchers (such as DABCYL, TAMRA, IOWA BLACK™ BLACK HOLE QUENCHER®-1, BLACK HOLE QUENCHER®-2) that are commercially available (IDT Inc.).

The new binary probe-based technology requires synthesis of only two short DNA, RNA, chimeric or oligonucleotides with specific analyte-binding arms for each different probe. Standard desalting provides sufficient purity for the oligonucleotides of such lengths. All other components of the probe, such as the double labeled fluorescent molecular beacons are universal for all assays. If applied for analysis of many different single nucleotide polymorphisms (SNPs), out of several million existing in human genome, the new approach will offer increased accuracy and the ability to work at moderate physiologic conditions. Since DNA-RNA and DNA-DNA hybrids have different structural parameters, the binary constructions should be customized for RNA in order to obtain highly specific and sensitive recognition of RNA targets.

Further details regarding standard methods of making and using MBs are well established in the literature and MBs are available from a number of commercial reagent sources. Further details regarding methods of MB manufacture and use are found, e.g., in Leone et al. (1995) Nucleic Acids Res. 26:2150-2155; Tyagi and Kramer (1996) 14:303-308; Blok and Kramer (1997) Mol Cell Probes 11:187-194; Hsuih et al. (1997) J Clin Microbiol 34:501-507; Kostrikis et al. (1998) Science 279:1228-1229; Sokol et al. (1998) Proc. Natl. Acad. Sci. U.S.A. 95:11538-11543; Tyagi et al. (1998) Nature Biotechnology 16:49-53; Bonnet et al. (1999) Proc. Natl. Acad. Sci. U.S.A. 96:6171-6176; Fang et al. (1999) J. Am. Chem. Soc. 121:2921-2922; Marras et al. (1999) Genet. Anal. Biomol. Eng. 14:151-156; and Vet et al. (1999) Proc. Natl. Acad. Sci. U.S.A. 96:6394-6399. Additional details regarding MB construction and use is found in the patent literature, e.g., U.S. Pat. No. 5,925,517 (Jul. 20, 1999) to Tyagi et al.; U.S. Pat. No. 6,150,097 to Tyagi et al (Nov. 21, 2000) and U.S. Pat. No. 6,037,130 to Tyagi et al (Mar. 14, 2000), The entire contents of these publications are hereby incorporated by reference as if fully set forth herein.

MBs are robust reagents for detecting and quantitating nucleic acids, even in real time (e.g., MBs can be used to detect targets as they are formed). A variety of commercial suppliers produce standard and custom molecular beacons, including Chruachem (chruachem.com), Oswel Research Products Ltd. (UK; oswel.com), Research Genetics (a division of Invitrogen, Huntsville Ala. (resgen.com)), the Midland Certified Reagent Company (Midland, Tex. mcrc.com) and Gorilla Genomics, LLC (Alameda, Calif.). A variety of kits which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com). The entire contents of these publications are hereby incorporated by reference as if fully set forth herein. Also the entire contents of U.S. Pat. No. 6,548,254 are hereby incorporated by reference as if fully set forth herein.

As with the MB-binding probes, kits can be made having the truncated dye-binding probe (without analyte-binding arms) so that the user can customize the probe for his or her own use. Alternatively diagnostic kits can be prepared having the full probe with analyte-binding arms (and optional structure stabilization arms) that are complementary and hybridize with high specificity to a known analyte.

The dye-binding probes can also be used in hybridization assays to detect a known analyte in a heterogeneous mixture of nucleotides. The assay is basically the same as that for molecular beacon probes. The dye to which the probe binds fluoresces at a low level when free in solution and at a high level when bound to the probe. The probe and the dye are mixed together and a background level of fluorescence is determined. The sample is then added to the mixture which is maintained for a sufficient period of time and under predetermined reaction conditions to allow the analyte to hybridize to the analyte-binding arms on the probe, and for the probe to bind to and activate the dye. It is determined that the analyte is present in the sample if the level of fluorescence of the dye increases above the background level. As before, more than one probe can be used to detect more than one different analyte in a single sample.

Fluorescent Oligonucleotide Tandems for Identifying Nucleic Acid Analytes

We have discovered an assay called the fluorescent oligonucleotide tandem (FOT) method, which allows fluorescent analysis of SNPs in nucleic acid analytes at room temperature using fluorophore- and a quencher-conjugated oligonucleotides that hybridize to analyte DNA, leaving a 5 nucleotide gap containing the SNP site between the quencher and fluorophore moieties. The oligonucleotides bind to the analyte forming a complex in which the fluorophore and the quencher moieties dangle in the pentanucleotide gap separating them. The fluorescence of the fluorophore is quenched in this complex. In the next step, four gap-filling pentanucleotides containing A, C, G or T at the position of interest (the SNP position) are added in four separate samples. Only the fully complementary pentanucleotide stably hybridizes to the gap thereby increasing fluorescence of the solution and indicating which of the 4 nucleotides is at the SNP site. Unlike conventional hybridization techniques this method avoids precise temperature control and enzyme-mediated steps for accurate SNP determination.

To make the FOT probe two oligonucleotides are designed that are complementary to different regions of the single stranded DNA/RNA analyte, which regions are separated from one another by a 4-7 nucleotide gap, preferably a 5 nucleotide gap as was used for the present experiments. Routine experimentation will determine the optimum gap size for the analyte and probe being used/designed. A first oligonucleotide strand is conjugated to a fluorophore at one end of the molecule that dangles into the gap when the first oligonucleotide strand hybridizes to the analyte. The second oligonucleotide strand is conjugated to a quencher that likewise dangles into the gap when the second oligonucleotide strand hybridizes to the analyte. FIG. 1, middle. If the fluorophore is on the 5' end of the first oligonucleotide, then the quencher must be attached to the 3' end of the second oligonucleotide, and visa versa. The fluorophore is quenched in this complex due to the close proximity of the dye molecules to each other. Hybridization of a short oligonucleotide, preferably a pentanucleotide, complementary to the gap completes the DNA double helix thereby causing the fluorophore and the quencher to shift to the opposite sides of the helix (FIG. 1A, right). This shift results in an increase in fluorescence that can be detected. A single base mismatch in the gap region dramatically reduces the stability of the complex, because one base miss-pairing eliminates about 20% of the total affinity of the pentanucleotide to the gap (FIG. 1A, left).

FOT complexes used in this study are shown in FIG. 2. The DNA analyte structure of the template for making FOT5-1T is SEQ ID NO. 5, which corresponds to all of the nucleotide sequence of *Francisella tularensis* 16S rRNA *F. tularensis* is a potential biological weapon agent and a highly infectious bacterium. rRNA, being a naturally amplified sequence, is ideal target molecules for detection systems. In the present study commercially available 5'-end fluorescein (FAM) and 3'-end DABCYL modified oligonucleotides were used as a fluorophore and quencher respectively for the proof-of-concept experiments (FIG. 2, left panels).

We studied fluorescence response of FOT5-1T (indicated as the wild-type analyte) to varying concentrations of four pentanucleotides containing nucleotide variations in the middle position (FIG. 2). A substantial increase in the fluorescence was observed only in the presence of complementary GCACG. However, some increase in emission intensities was found in the presence of high concentrations of mismatched GCGCG as well. This can be explained by the G-T wobble base-pair formation between third guanine of GCGCG and the thymidine in the middle position of the gap.

The highest difference of the fluorescence intensities was found in the presence of 1.25 mM pentanucleotides. Therefore, this concentration was used as the optimum concentration for the calculation of the discrimination factors (DFs) (Table 1). We studied analytes containing all possible substitutions in the middle position of the gap using the FOT approach (Table 1). The DFs are indicated as "VH" (very high) for those pentanucleotides that triggered no fluorescence significantly above the background. In all cases DFs for mismatched pentanucleotides were higher than 1. In five out of eighteen cases fluorescent intensities for mismatched petanucleotides did not significantly exceed the background fluorescence resulting in very high DFs. These data demonstrate that FOT enables accurate mismatch recognition at room temperature and therefore is an excellent instrument for SNP typing. The lowest DF (1.8±0.14) for FOT5-1G and mismatched GCACG can be explained by A-G wobble base pair formation.

In order to prove the general applicability of the approach we studied the fluorescent response of an FOT of different design (FIG. 4) consisting of a 40 nucleotide analyte template that is a fragment of *F. tularensis* 16S rRNA, and fluorophore- and quencher bound oligonucleotides that hybridize to the template leaving five-nucleotide gap between the FAM and DABCYL groups (FIG. 4A). Similar to the experiments describe above for FOT5-1, FOT5-2 (SEQ ID NO 6) was incubated at different concentrations of either pentanucleotide fully complementary to the gap nucleotides on the analyte or pentanucleotides containing single substitution in the middle position (FIG. 2B). A substantial increase in fluorescence was found only in the presence of complementary GGTAA (FIG. 4). The mismatched pentanucleotides triggered no fluorescence significantly greater the background at the concentrations of 5 mM resulting in very high discrimination factors. The results of this experiment demonstrate general applicability of the FOT approach.

One embodiment is directed to an assay in which: 1. identifying a known SNP in a chromosome in the genome of an animal, 2. obtaining an single stranded analyte fragment from human or an experimental animal which fragment comprises a part of the chromosome having the known SNP identified in step 1, 3. identifying a 5 nucleotide long target analyte sequence in the analyte fragment, in which the position of the known SNP is at the center (the number 3 nucleotide), 4. designing a fluorescent oligonucleotide tandem probe of claim 55 that binds to the target analyte, 5. designing four oligonucleotides from 4-7 nucleotides long of known sequence in which the nucleotides in all positions except one are complementary to respective nucleotides in the target sequence, 6. mixing the analyte with the first and second oligonucleotide probes under conditions that permit hybridization, 7. determining the amount of fluorescence in the mixture of step 6, to obtain a baseline fluorescence, 8. adding one of the four penta-oligonucleotides probes under conditions that permit hybridization, 9. measuring the fluorescence of the mixture in step 8, 10. determining that a penta-oligonucleotide has bound to the target sequence and is fully complementary to the target sequence if the fluorescence determined in step 9 is significantly greater than the baseline fluorescence, 11. if the penta-oligonucleotide of step 10 is determined to be fully complementary to the target sequence, then identifying the nucleotide at the center position of the target sequence as that corresponding to the nucleotide at the center position of the penta-nucleotide added in step 6, and 12. determining whether the nucleotide at the center position of the target sequence represents an SNP by comparing it with the known SNP, and 13. if the penta-oligonucleotide is not fully complementary to the target sequence, then washing out the penta-oligonucleotide and adding another penta-oligonucleotide before repeating steps 8-12.

Figure 5:
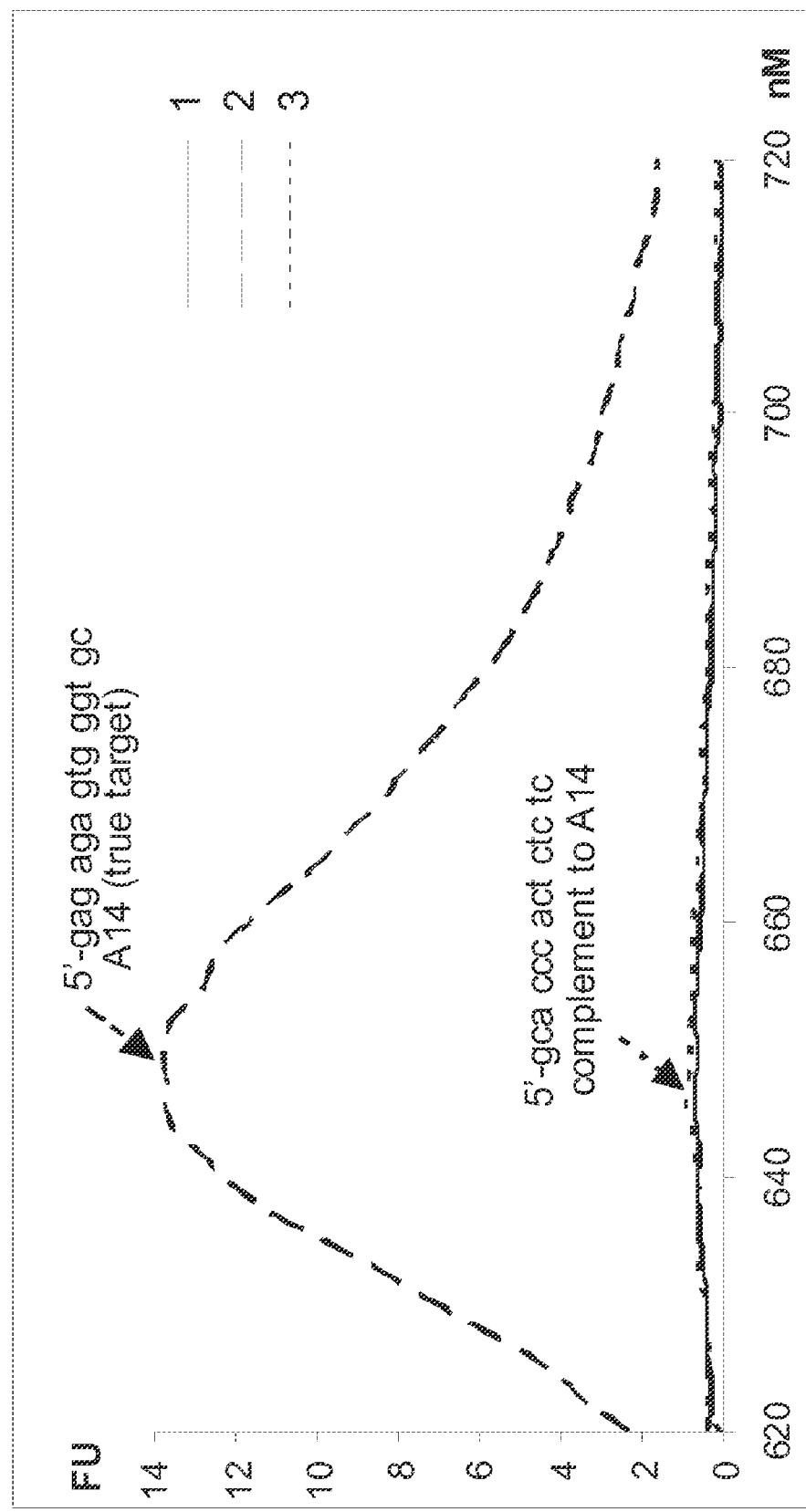
FIG. 5 Binary Malachite Green Aptamer probe increases its fluorescence upon hybridization to DNA analyte. The emitting spectra of MG (2 µM) and biMGA (1 µM) was recorded in the absence (1) or presence (2, 3) of 2 µM A14; curve (3) in the presence of 4 µM DNA competitor, which is complementary to A14.

FOT taken together with combinatorial approach can allow for more complex analysis of a five-nucleotide fragment. The ideology of the approach is similar to that of sequencing by hybridization. The procedure involves incubating the FOT (analyte/oligonucleotide complex) with five pentanucleotide libraries in five separate mixtures. Each pentanucleotide library consists of four pentanucleotides containing all possible nucleotide variants at one of the five possible positions (FIG. 5). Only the sample incubated with the library that includes all possible base variations at the position complementary to the SNP site will have increased fluorescence, because this is the only library that contains the fully matched petanucleotide. For example, FOT5-1C contains a single nucleotide substitution (the "C" nucleotide) in the $3^{rd}$ position of the pentanucleotide gap on the analyte (CGCGC). Among the five pentanucleotide libraries only the $3^{rd}$ library (GC-NCG), which contains complementary GCGCG, triggered fluorescence above the background (FIG. 5, dark bars). A similar result was found for FOT5-1T($G^4$/A) (which is CGTAC) and FOT5-1T($C^5$/T) (which is CGTGT), containing substitutions in the $4^{th}$ and $5^{th}$ positions, respectively (FIG. 5, white and gray bars). Theoretically, resequencing of the gap is possible using combinations of pentanucleotide libraries or the separate 1024 possible pentanucleotides.

The FOT assay allows accurate mismatch recognition at room temperature and thus does not require precise temperature control for allele discrimination and is cheap. The S/B ratio can be optimized by changing the chemical nature of the linkers between the dyes and the oligonucleotide moieties using routine methods known in the art. For example, rigid linkers, such as those containing double and triple bonds, can bring the dye moieties closer to each other in the gap; thus allowing more efficient quenching.

A Scheme for Micro-Array Assay Based on Fluorescent Oligonucleotide Tandems

A new assay has been discovered that can be used for typing several thousands of human SNPs using microchip based technology. At the fist stage the genetic material, which can be a DNA taken from a few cells of an individual, is PCR amplified with a set of several thousands pairs of different primers in one test-tube. The design of the each primer pair allows amplification of a unique 30-300 nucleotide fragment of the genome that contains an SNP site.

At the second stage the mixture of single stranded DNA material (analytes amplified by the different primers) is annealed to a mixture of several thousands of different fluorophore-conjugated oligonucleotides, a component of fluorescent DNA tandems. The design of each fluorescent oligonucleotide allows it to hybridize to the analyte 2-3 nucleotides away from the putative SNP site.

A microarray is made of oligonucleotides conjugated to quenchers that hybridize to the analyte at a second position flanking the five-nucleotide target sequence on the side opposite the fluorophore-conjugated oligonucleotide so that each individual analyte fragment hybridizes to definite spot on microarray chip. DNA micro-array chip production and hybridization procedure are well established. The total number of spots available for quencher-bound oligonucleotides is about 3000, which corresponds to the number of known SNPs in the human genome. At the third stage the analyte-fluorophore-conjugated oligonucleotides are incubated with the microarray under conditions that permit hybridization. If there is hybridization at this step, the fluorescence of the fluorophore is quenched by the quencher and fluorescence signal is low.

At the next step the chip is incubated with a solution of the same penta-oligonucleotides of known structure or a mixture of penta-oligonucleotides, such as the libraries described above. The fluorescent signal is increased at the spots of the microarray chip that contain penta-oligonucleotide target sequences on the analyte that are fully complementary to one of the added penta-oligonucleotides. The chip reader detects the signal, and spatial software analyses the data. Then the chip is washed in mild conditions in such a way that penta-oligonucleotides are removed from the chip while fluorophore- and quencher-conjugated oligonucleotides are still bound or hybridized to the analyte. The rejuvenated microchip is then incubated with a different penta-oligonucleotide or library of pentanucleotides. And the process of data collection is repeated. The number of incubations with different penta-oligonucleotides can be as many as 1024, since there are 1024 statistically possible penta-oligonucleotides. However, the number of incubations can be reduced by using a mixture of penta-oligonucleotides in a library at each incubation step.

Other Binary Probes

Other probes derived from BDP can be designed. These probes aim to bind a fragment of the reporter molecules (such as a molecular beacon MB or dye) longer than 16 nucleotides. This will allow a larger separation of fluorophore from the quencher when the probe is bound to DNA analyte, thus increasing S/B and improving the sensitivity of the probes.

One approach to achieve this is to design a BDP with MB binding arms that are 17 nucleotides long in strand (A) and 18 nucleotides long in strand (B). (FIG. 13A, top.) The MB binding arms of BDP20/35 strand A=SEQ ID NO. 7; The MB binding arms of BDP20/35 strand B=SEQ ID NO. 8. Certain embodiments are directed to the truncated BDP20/35 probe having the two MB binding arms, to which a linker and analyte-binding arm can be customized and added, and to MB-G. This probe binds to 35 nucleotides of MB-G (SEQ ID NO. 9) in the presence of analyte. MB-G has two (SSA) structure stabilization arms added to the two ends of the MB-binding arms to prevent MB-BDP self-association in the absence of DNA analyte. Another embodiment is directed to this probe and one to the MB-G. The length of stem 3, stem 4 and stem 5 should be optimized to allow analyte dependent formation of the quaternary HJ-like structure (FIG. 13A, bottom). Certain embodiments are directed to BDP with MB binding arms that are each about 8 nucleotides to about 20 nucleotides long to optimize separation of fluorophore from quencher.

Figure 13:
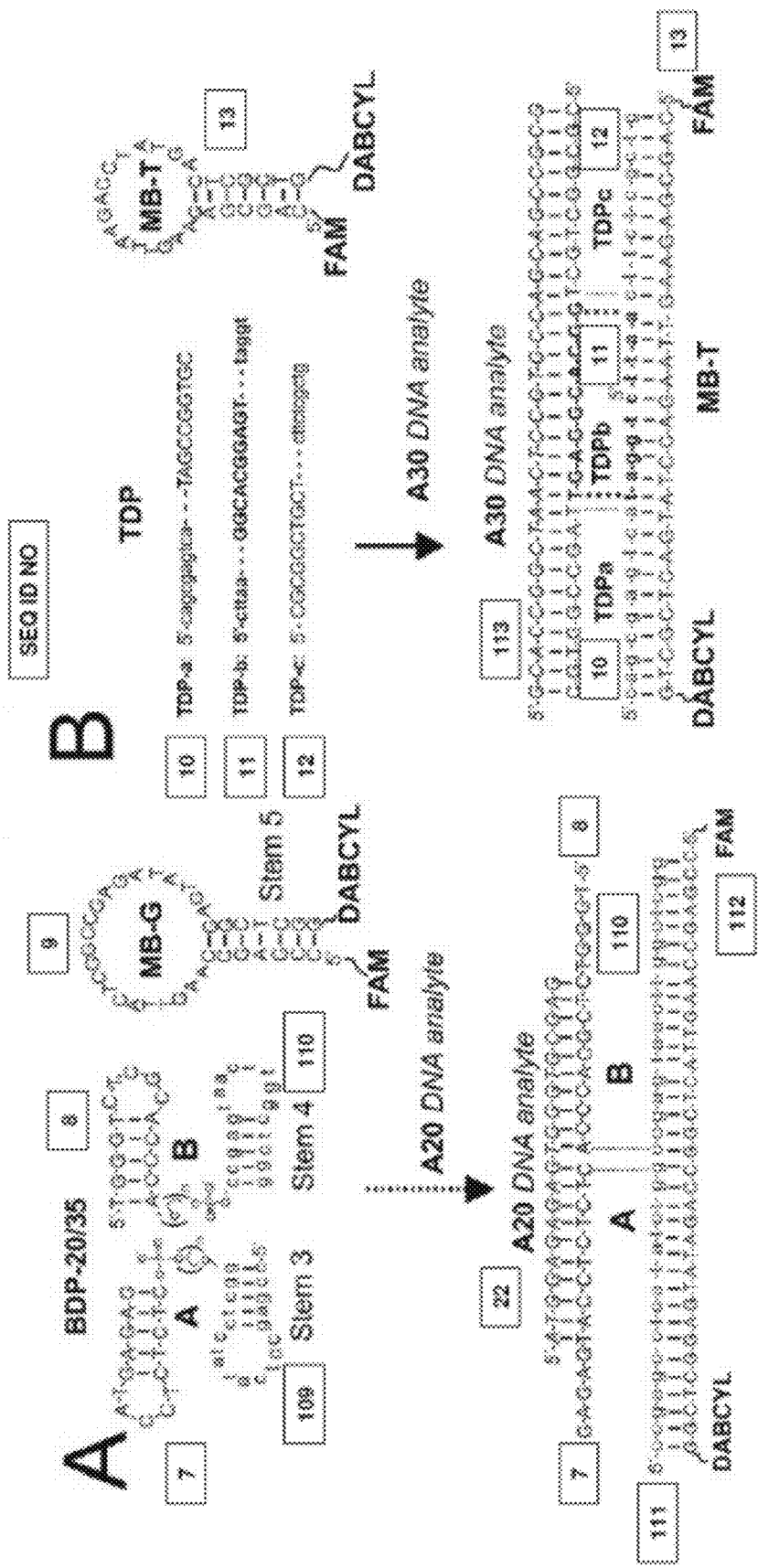
FIG. 13 :DNA branched motifs for highly selective recognition of nucleic acids. (A) BDP forms Holliday junction in the presence of DNA analyte. (B) Tripartite DNA probe (TDP) forms double crossover motif in the presence of DNA analyte.

A tripartite DNA probe (TDP) is another possible instrument for nucleic acids analysis. The probe will consist of three DNA strands (TDPa, TDPb, TDPc) and a MB (MB-T) (FIG. 13B, top). In the presence of a 30 nucleotide analyte the TDP forms the double-crossover structure (FIG. 13B, bottom). In the double-crossover complex the quencher (DABCYL) is removed by 30 nucleotides (10.8 nm) from fluorescein. The greater separation of fluorophore from quencher increases fluorescent. The example shown in FIG. 13 illustrates the basic probe design of a TDP. TDPa, TDPb, and TDPc of the probe in FIG. 13B correspond to SEQ ID NOs. 10, 11 and 12, respectively. MB-T corresponds to SEQ ID NO. 13. The TDP should be sensitive to single mismatches located at any position of 30 nucleotide analyte.

Figure 14:
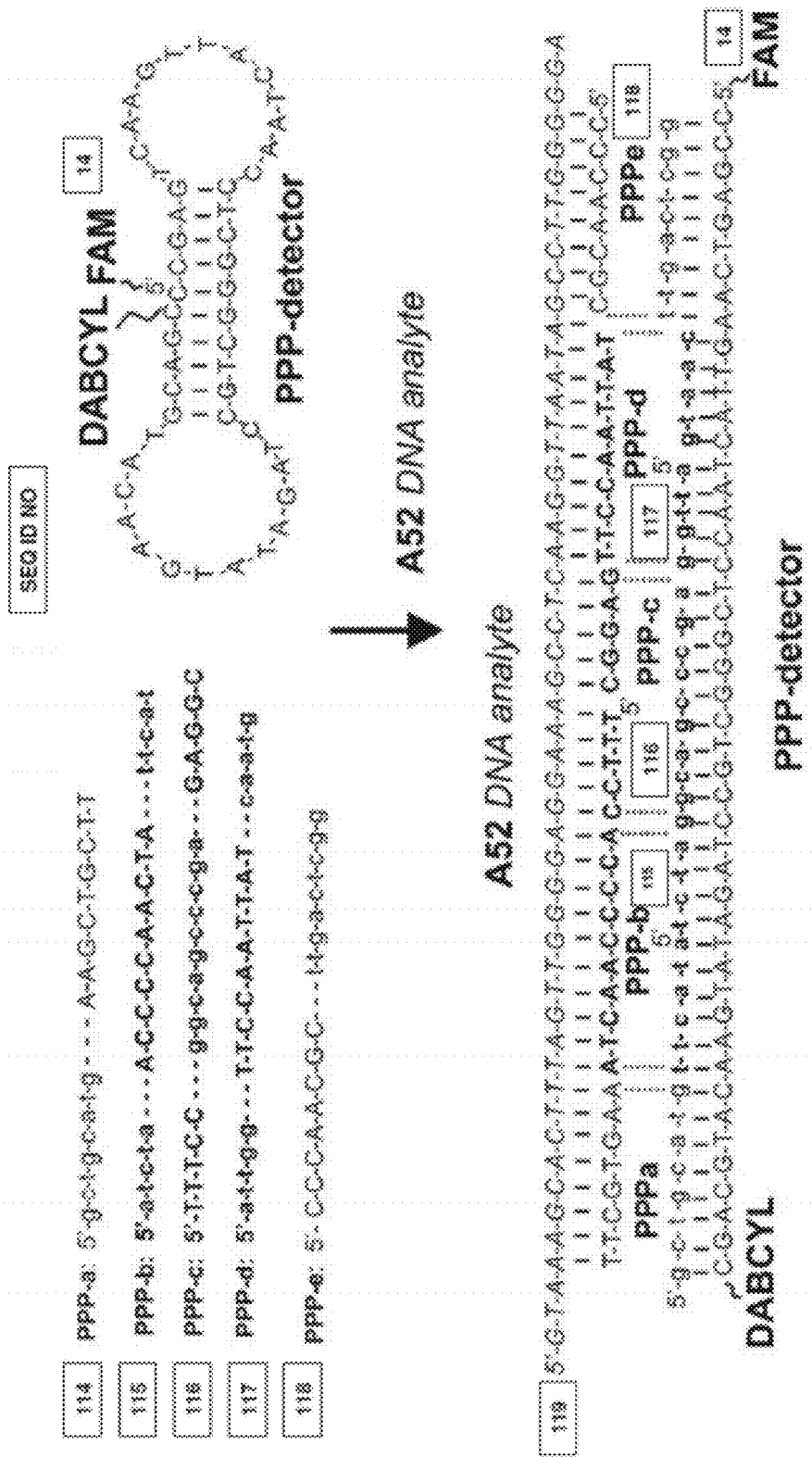
FIG. 14 Pentapartate probe for nucleic acid analysis. PPP binding arms are in low case.

To further improve the sensitivity and increase DFs of mismatched analytes one can attach structure stabilization arms to form stem loops in the analyte binding fragments, for example in TDPa and TDPc. A similar principle can be used to make penta-partite probes (PPP, FIG. 14). The conventional MB can be substituted with more a stable structure like a PPP-detector, which is a fluorophore and quencher-conjugated oligonucleotide. It contains terminal pentanucleotide fragments complementary to two adjusting internal domains. When free in solution, the PPP-detector (SEQ ID NO. 14) exists as a dumbbell-shaped structure (FIG. 14). The PPP-detector is preferable to a MB because it forms two (instead of one) stems; these stems allow higher stability and more efficient fluorescence quenching. As with the other binary probes, the analyte arms are the only feature that needs to be customized; the rest of the probe can be used without modification regardless of the analyte. Thus the BNP of the present invention is an inexpensive tool in case of multiplex nucleic acid analysis. Certain embodiments of the invention are directed to tripartite DNA probes complexed with MBs or PPP-detectors.

Figure 15:
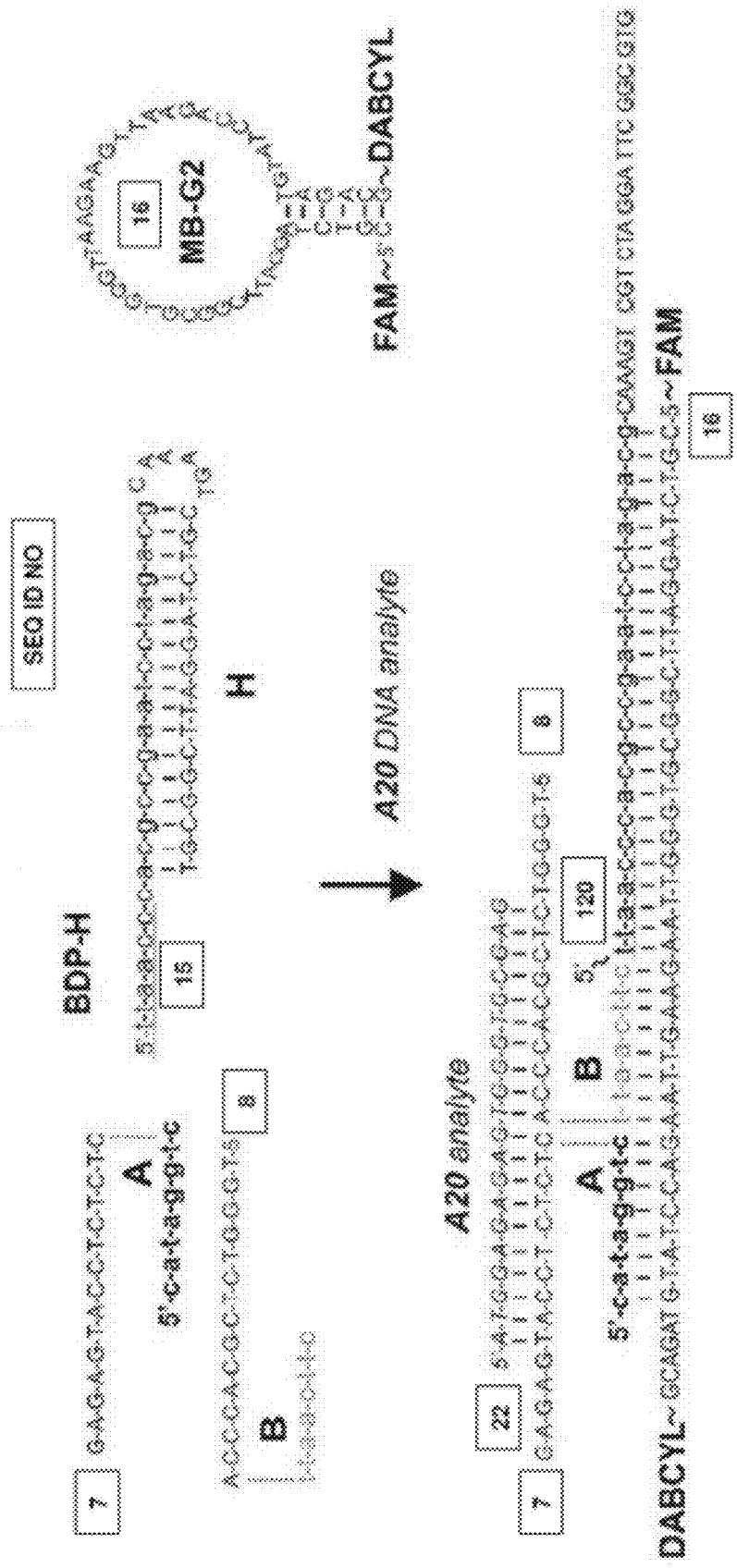
FIG. 15 Four-way junction-like structure stabilized by interaction with DNA hairpin H. MB binding arms are in low case.

Alternatively, MB Hairpin probes can be made such that the fluorophore can be removed to a distance of 40 and more nucleotides from the quencher upon complex formation with the analyte using probes such as those depicted in FIG. 15. To make a MB hairpin, a DNA hairpin H will be made and added to a mixture containing molecular beacons and BDP. In the absence of DNA analyte the system is caught in kinetic trap because the 18 nucleotide long stem of the hairpin H protects it from hybridizing to MB-G2. The sequence of H is set forth in SEQ ID NO. 15. Addition of the DNA analyte allows cooperative hybridization of strands A and B and the DNA hairpin H to MB-G2 thereby increasing fluorescence. An embodiment of the invention is MB-G2, the sequence of which is set forth in SEQ ID NO. 16. It should be noted that the hybridization process in "MB-hairpin" probe can not be reversed to the dissociated state by elimination of the analyte. This is because the 24 nucleotide H-MB-G2 hybrid is stable at the conditions used. The length of stems and loops can be varied in the structure of MB-G2 and H. Similarly the length of the MB binding arms of strands A and B can be changed in order to achieve optimum analyte dependent fluorescence of the probe using routine experimentation. The MB binding arms of BDP-H, binary DNA hairpin) are shown in FIG. 15. Quaternary complex formation can be verified by comparing PAGE mobility of the starting strands and the final complex. Certain other embodiments are directed to the MB-Hairpin probes described above.

Once the structures of the probes are optimized they can be easily adjusted for recognition of analytes of any sequence. The change in analyte-binding arms will be the only alteration required.

EXAMPLES

Example 1

Binary DNA Probes
A. Materials:
DNAse/RNAse free water was purchased from ICN (Costa Mesa, Calif.) and used for all buffers, and for stock solutions of oligonucleotides. Oligonucleotides were custom-made by Integrated DNA Technologies, Inc. (Coralville, Iowa) and were used as received. Fluorescent spectra were taken on a Perkin-Elmer (San Jose, Calif.) LS-55 Luminescence Spectrometer with a Hamamatsu Xenon lamp. Experiments were performed at the excitation wavelength of 485 nm and emission scan of 500-550 nm. The emitting intensities at 517 nM were taken for the calculation of the discrimination factors. The data of four independent experiments were processed using Microsoft Excel.
B. Discrimination factors (DFs) for BDPs
The solutions of MB1 (20 nM), strands A and B (500 nM for BDP10/8sl and BDP10/8sl $F.\ tul$ or 200 nM for BDP8/8 and BDP10/8) in 120 µl of 50 mM $MgCl_2$, 10 mM Tris HCl, pH 7.4 were incubated in the presence of either 40 nM A20 or one of the single base-substituted oligodeoxynucleotide 15 min at room temperature followed by fluorescent emission spectrum measurements. The fluorescence intensities at 517 nM were taken for the calculation of the DFs.
C. MB2 Assay
Solutions of 20 nM MB2 (FAM-CTC GCA CCC ACT CTC TCC ATG CGA G-TAMRA) (SEQ ID NO: 4) in 120 µl of 100 mM KCl, 1 mM $MgCl_2$, 10 mM Tris HCl were incubated in the presence of either 40 nM A20 or one of the single base-substituted oligodeoxynucleotides 15 min at room temperature followed by fluorescent emission spectrum measurements. The fluorescence intensities at 517 nM were taken for calculation of the DFs.
D. A20 Concentration Dependence Measurements
MB1 (20 nM) and strands A and B (600 nM each) of BDP10/8sl were incubated in the absence or presence of 500 nM A20-4 (ATG TAG AGA GTG GGT GCG AG) (SEQ ID NO: 20) at variable A20 concentrations. Fluorescence intensities at 517 nM were taken in four independent experiments.

Example 2

Binary Malachite Green Binding Probe
A. Materials.
DNAse/RNAse free water was purchased from ICN (Costa Mesa, Calif.) and used for all buffers, and for stock solutions of olionucleotides. Malachite Green was purchased from Sigma-Aldrich Co (Milwaukee, Wis.). Oligonucleotides were custom-made by Integrated DNA Technologies, Inc. (Coralville, Iowa) and were used as received. The structures of the oligoribonucleotides were as follows: 5'-GCACCCA UU UCCC GA C UGG (SEQ ID NO: 95) and 5'-CCAG G UAA CGA AU GGA UU CUC UCU C (SEQ ID NO: 96). The structure of A14 DNA analyte was gagagag tgggtgc (SEQ ID NO: 52) while the structures of single base substituted oligodeoxyribonucleotides are presented in the Table 2.
B. Binary Malachite Green Aptamer Probe.
MG (2 µM) and two RNA strands of biMGA probe (1 µM each) were mixed in 5.3 ml of the buffer containing 50 mM TrisHCl pH 7.4, 140 mM NaCl, 5 mM KCl, 1 mM $MgCl_2$. The solution was distributed into 44 tubes (120 µl in each tube) followed by addition of A14 or one of the single base substituted A14 analogs to the final concentration of 2 µM. The samples were incubated 15 min at room temperature. Fluorescent spectra were taken on a Perkin-Elmer (San Jose, Calif.) LS-55 Luminescence Spectrometer with a Hamamatsu Xenon lamp. Experiments were performed at the excitation wavelength of 610 nm and emission scan of 620-720 nm. The emitting intensities at 648 nM were taken for the calculation of the discrimination factors. The data of four independent experiments were processed using Microsoft Excel.

C. Binary Malachite Green Aptamer for Recognition of DNA Domains Separated by One or Two Nucleotides.

In order to evaluate the ability of biMGA probe to recognize 7 nucleotide DNA fragments separated on a DNA molecule we compared fluorescence intensities of biMGA probe in the presence of A14 DNA analyte and A15 gagagag t tgggtgc (SEQ ID NO: 97) and A16 gagagag tt tgggtgc (SEQ ID NO: 98) DNA analytes (FIG. 3). A15 and A16 trigger higher fluorescence intensities then A14, probably, because of sterically more relaxed conformation of the biMGA-DNA analyte complex in the case of one or two nucleotide insertion between the recognition sites.

Example 3

Fluorescent Oligonucleotide Tandems
Analysis of the Gaps of Different Length.

First we examined the fluorescence response of tetra-, penta- and hexanucleotide gaps to the presence of gap-filling oligonucleotides (FIG. 2). It was found that all FOTs tested increased fluorescence upon addition of cognate oligonucleotides, i.e. oligonucleotides fully complementary to the analyte gap sequence where the SNP site is. Fully complementary binding of the gap-filling oligonucleotide to the analyte gap region causes the formation (or completion) of a double helix that in turn increases fluorescence by moving or shifting the fluorophore away from the quencher. (FIG. 2, right panels). The signal-to-background (S/B) ratios were 1.2, 2.0 and 2.5 for tetra-, penta- and hexanucleotide gaps, respectively. We concluded that penta- and hexanucleotide gaps were the most suitable for FOT approach. For further experiments we chose five-nucleotide gaps since sensitivity of pentanucleotide to single base mismatch was substantially higher than that of hexanucleotides (data not shown).

B. Materials.

DNAse/RNAse free water was purchased from Fisher Scientific Inc. (Pittsburgh, Pa.) and used for all buffers, and for stock solutions of oligonucleotides. Oligonucleotides were custom-made by Integrated DNA Technologies, Inc. (Coralville, Iowa) and were used as received. Fluorophore and quencher labeled oligonucleotides were HPLC purified.

C. Pentanucleotide Concentration Dependence.

The solutions of DNA analyte in complex with the fluorophore and the quencher oligonucleotides were prepared by combining of 10 µl of the 100 µM DNA analyte, 9 µl of the 100 µM FAM conjugated oligonucleotide, and 11 µl of the 100 µM quencher conjugated oligonucleotide in a 10 ml buffer (50 mM MgCl$_2$, 10 mM Tris HCl pH 7.4). The analyte and the quencher oligonucleotides were added in excess amount to reduce the background fluorescence the fluorophore oligonucleotide. After 18-20 hours of incubation at room temperature the solution was split into 10 separate test tubes, 120 µl in each. A different concentration of the pentanucleotide was added to each tube to the final concentrations of 0.16 µM, 0.31 µM, 0.63 µM, 1.25 µM, 2.5 µM, 5.0 µM, 10 µM, 20 µM, and 40 µM. The samples were incubated at room temperature for 1 hour followed by recording of the fluorescent spectra on a Perkin-Elmer (San Jose, Calif.) LS-55 Luminescence Spectrometer with a Hamamatsu Xenon lamp. Experiments were performed at the excitation wavelength of 485 nm and emission scan of 500-550 nm. The average fluorescence intensities at 517 nM of three independent measurements were plot against the pentanucleotide concentration. Note that long incubation times (18 hours for fluorophore and quencher incubation with a template and 1 hour for incubation with short oligonucleotides) were used to succeed better data reproducibility. At the same time the expected effect, the higher fluorescence in the presence of only fully complementary pentanucleotide, was observed immediately after mixing of the oligonucleotides.

D. Determination of Discrimination Factors.

The solutions of DNA analyte in complex with the fluorophore and the quencher oligonucleotides were prepared as described above. The correspondent pentanucleotides were added to the final concentration of 1.25 mM for FOT5-1 or 5 mM for FOT5-2. The control mixtures contained no pentanucleotides. The fluorescent emission spectra were recorded after 1 hr of incubation at room temperature. Fluorescence intensities at 517 nm were used for the calculation of the DFs. The data of three independent experiments were processed using Microsoft Excel.

E. Identification of SNP Position within the Gap.

The solutions of DNA analytes in complex with the fluorophore and the quencher oligonucleotides were prepared as described above and split into 6 tubes for each analyte. The pentanucleotide libraries NCTCG, GNTCG, GCNCG, GCTNG, or GCTCN (where N represents machine mixture of A, G, C and T) were added to the final concentration of 1.25 mM. Control sample did not contain pentanucleotides. After 1 hr of incubation at room temperature the fluorescent emission spectra were recorded. Fluorescence intensities at 517 nm are represented in FIG. 5 after subtraction of the background fluorescence.

Example F. Flexible Linkers

The "Int" linkers below, referred to by the manufacturer Integrated DNA technology as "spacers" can be used to make the probes of the present invention.

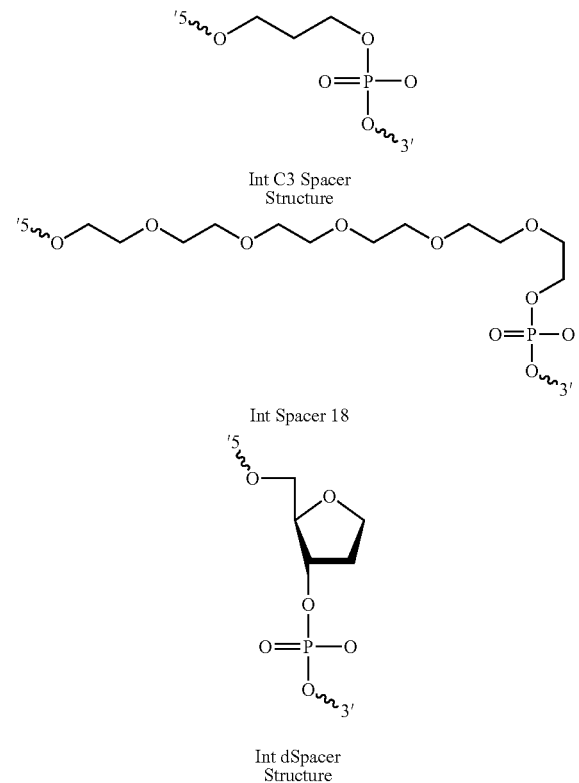

Int C3 Spacer Structure

Int Spacer 18

Int dSpacer Structure

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A non-naturally occurring, noncatalytic oligonucleotide probe for detecting a single-stranded oligonucleotide analyte, comprising two oligonucleotide strands, wherein
    (1) a first oligonucleotide strand comprises:
        a. at its 5'-terminus a reporter binding arm that is complementary to and is capable of selectively hybridizing with a reporter, and
        b. at its 3'-terminus, a first analyte binding arm that is complementary to and is capable of selectively hybridizing with a first region of the oligonucleotide analyte, and
    (2) a second oligonucleotide strand comprises:
        a. at its 3'-terminus a reporter binding arm that is complementary to and is capable of selectively hybridizing with a nucleotide sequence in the reporter, and
        b. at its 5'-terminus, a second analyte binding arm that is complementary to and is capable of selectively hybridizing with a second region of the oligonucleotide analyte.

2. The probe of claim 1, wherein the analyte binding arms bind to the reporter binding arms on the respective first and second strands through a linker.

3. The probe of claim 2, wherein the linker is part of the analyte binding arms and the reporter binding arms on the respective first and second strands.

4. The probe of claim 2, wherein the linker comprises a molecule added between the analyte binding arms and the reporter binding arms on the respective first and second strands.

5. The probe of claim 4, wherein the linker is a member selected from the group comprising an oligoethylene glycol, one or more nucleic acids, int c3 linker, int linker 18, and int linker.

6. The probe of claim 1, wherein the oligonucleotide probe comprises DNA and the oligonucleotide analyte comprises DNA.

7. The probe of claim 1, wherein the oligonucleotide probe comprises RNA and the oligonucleotide analyte comprises RNA.

8. The probe of claim 1, wherein the oligonucleotide probe comprises DNA and RNA.

9. The probe of claim 1, wherein the analyte binding arms each comprise from about 6 to about 20 nucleotides.

10. The probe of claim 1, wherein the reporter binding arms are each from about 4 to about 20 nucleotides long.

11. The probe of claim 1, wherein about 3-20 additional nucleic acids are added to the free end of the analyte binding arms of the first and second strands, which additional nucleic acids are complementary to and capable of hybridizing with nucleic acids in the respective analyte binding arms to form a stem-loop structure when the first and second strands are not hybridized to the analyte.

12. The oligonucleotide probe as in claim 1, wherein from about 3 to about 20 additional nucleotides are added to the free end of the reporter binding arms of the first and second strands, which additional nucleic acids are complementary to and capable of hybridizing with nucleic acids in the respective reporter binding arms to form a stem-loop structure when the first and second strands are disassociated from one another.

13. The probe of claim 1, wherein the reporter is a molecular beacon.

14. The probe of claim 13, wherein the molecular beacon is a member selected from the group consisting of MB1 having SEQ ID NO: 3, MB2 having SEQ ID NO: 4, MB-G having SEQ ID NO: 9, MB-T having SEQ ID NO: 13, MB-G2 having SEQ ID NO: 16.

15. The binary DNA probe BD20/35, wherein the first strand comprises the sequence set forth in SEQ ID NO: 7, and the second strand comprises the sequence set forth in SEQ ID NO: 8.

16. The probe of claim 1, wherein the reporter binding arm on the first oligonucleotide strand is a molecular beacon binding arm comprising the sequence TTAACTTC and the reporter binding arm on the second oligonucleotide strand is a molecular beacon binding arm comprising the sequence CATAGGTC, and wherein the molecular beacon has the sequence set forth in SEQ ID NO: 1.

17. A non-naturally occurring, binary oligonucleotide probe for detecting a single stranded oligonucleotide analyte, the probe comprising two antiparallel oligonucleotide strands, wherein the first strand comprises:
    a) at its 5'-terminus an analyte binding arm,
    b) a first stem sequence on the first strand flanking the analyte binding arm, wherein the first stem sequence is complementary to a first stem sequence on a second strand,
    c) a dye-binding nucleotide sequence flanking the first stem sequence on the first strand, and
    d) at its 3'-terminus a second stem sequence on the first strand that is complementary to a second stem sequence on the second strand, and
    the second strand comprises:
    a) at its 3'-terminus an analyte binding arm,
    b) a first stem sequence on the second strand flanking the analyte binding arm, wherein the first stem sequence is complementary to the first stem sequence on the first strand,
    c) a dye-binding nucleotide sequence flanking the first stem sequence on the second strand, and
    d) at its 5' terminus a second stem sequence on the second strand that is complementary to the second stem sequence on the first strand.

18. The probe of claim 17, wherein the analyte binding arms, the dye binding arms and the first and second stems comprise DNA oligonucleotides, RNA oligonucleotides, or chimeras of DNA and RNA.

19. The probe of claim 17, wherein the analyte binding arms bind to the dye-binding arms on the respective first and second strands through a linker.

20. The probe of claim 19, wherein the linker comprises two nucleotides on the ends of the analyte binding arms and the reporter binding arms on the respective first and second strands through which the two arms are bound.

21. The probe of claim 19, wherein the linker comprises a molecule added between the analyte binding arms and the dye-binding arms on the respective first and second strands.

22. The probe of claim 21, wherein the linker a member selected from the group comprising an oligoethylene glycol, int c3 linker, int linker 18, and int linker.

23. The probe of claim 17, wherein the first and second strands hybridize to one another at the respective complementary first and second stem sequences when the probe is hybridized to the analyte.

24. The probe of claim 17, wherein from about 3 to about 20 additional nucleotides are added to the free end of the analyte binding arms of the first and second strands, which additional nucleic acids are complementary to and capable of hybridizing with nucleic acids in the respective analyte binding arms to form a stem-loop structure when the first and second strands are disassociated from one another.

25. The probe of claim 17, wherein the analyte binding arm on the first and the second strands is from about 6 to about 20 nucleotides long, making the total analyte binding region of the two strands from about 12 to about 40 nucleotides long, or from about 7 to about 10 nucleotides long, making the total analyte binding region of the two strands from about 14 to about 20 nucleotides long.

26. The probe of claim 17, wherein the first stem on the first strand is from 2 to 10 nucleotides long, and the first stem on the second strand corresponds in length and is complementary to the first stem on the first strand.

27. The probe of claim 17, wherein the second stem on the first strand is from 2 to 10 nucleotides long, and the second stem on the second strand corresponds in length to the second stem on the first strand.

28. The probe of claim 19, wherein the linker comprises one or more nucleic acids.

29. The probe of claim 17, wherein the dye-binding nucleotide sequences on the first and second strands bind to a triphenylmethane dye selected from the group consisting of 4-[(4-dimethylaminophenyl)phenyl-methyl]-N,N-dimethylaniline, bis(N-methylindolinyl), and Insulin labeled with 4-[(4-dimethylaminophenyl)phenyl-methyl]-N,N-dimethylaniline, bis(N-methylindolinyl).

30. The probe of claim 17, wherein the dye-binding nucleotide sequences on the first and second strands bind to a sulforodamine dye that is a member selected from the group consisting of PATENT BLUE VIOLET (Ethanaminium) and N-[4-[[4-(Diethylamino)phenyl](2,4-disulfophenyl)methylene]-2,5-cyclohexadien-1-ylidene]-N-ethyl-ethanaminium inner salt sodium salt [patent blue VF].

31. The dye-binding probe biMGA probe, wherein the first strand of the probe comprises SEQ ID NO: 2 and the second strand comprises the nucleotide sequence set forth in SEQ ID NO: 3.

32. A non-naturally occurring fluorescent oligonucleotide probe for detecting a single nucleotide polymorphism in a single-stranded oligonucleotide target analyte comprising:
a) a first oligonucleotide strand bound to a quencher, wherein the first strand is complementary to and capable of selectively hybridizing with a nucleotide sequence in a first region in the target analyte,
b) a second oligonucleotide strand bound to a fluorophore, wherein the second strand is complementary to and capable of selectively hybridizing with a nucleotide sequence in a second region in the target analyte, wherein the first and second strands are separated from one another by a 4-7 nucleotide gap when hybridized to the target analyte, which gap contains the single nucleotide polymorphism, and
c) a 4-7 nucleotide-long oligonucleotide that hybridizes to the target analyte in the gap, wherein binding of a fully complementary 4-7 nucleotide-long oligonucleotide generates a signal from the fluorophore.

33. The probe of claim 32, wherein the first and second strands are from about 10 to about 100 nucleotides in length.

34. The probe of claim 32, wherein the first and second strands of the probe comprise DNA oligonucleotides, RNA oligonucleotides, or chimeras of DNA and RNA.

35. The probe of claim 32, wherein the fluorophore is selected from the group consisting of fluorescein amidite, 2-[3-(dimethylamino)-6-dimethyliminio-xanthen-9-yl]benzoate, (2E)-2-[(2E,4E)-5-(2-tert-butyl-9-ethyl-6,8,8-trimethyl-pyrano[3,2-g]quinolin-1-ium-4-yl)penta-2,4-dienylidene]-1-(6-hydroxy-6-oxo-hexyl)-3,3-dimethyl-indoline-5-sulfonate, 6-carboxy-2',4,4',5',7,7'-hexachlorofluorescein, 4,5,6,7-Tetrachlorofluorescein, sulforhodamine 101 acid chloride succinimidyl ester, cyanine-Dyes, and Rhodamine 123 (hydrochloride).

36. The probe of claim 32, wherein the quencher is selected from the group consisting of BLACK HOLE QUENCHER-1®, BLACK HOLE QUENCHER-2®, IOWA BLACK QUENCHERS®, and 4-([4-(Dimethylamino)phenyl]-azo)-benzoic acid succinimidyl ester.

37. A diagnostic binary oligonucleotide probe hybridization assay kit to detect a single stranded nucleic acid analyte in a sample containing a heterogeneous mixture of nucleic acids, the kit comprising:
A. the probe of claim 1, and
B. a reporter that binds to the reporter binding arms on the first and second strands of the probe.

38. A kit for making a non-naturally occurring binary oligonucleotide probe for detecting a single stranded nucleic acid analyte, comprising:
(1) two antiparallel oligonucleotide strands, wherein
the first oligonucleotide strand comprises:
a. at its 5'-terminus a reporter binding arm that is complementary to and is capable of selectively hybridizing with a reporter, and
the second oligonucleotide strand comprises:
a. at its 3'-terminus a reporter binding arm that is complementary to and is capable of selectively hybridizing with the reporter, and
(2) the reporter that binds to the reporter binding arms on the first and second strands of the probe.

39. The assay of claim 37, wherein the analyte is DNA, and the analyte binding arms and the reporter binding arms of the oligonucleotide probe are DNA oligonucleotides.

40. The assay of claim 37, wherein the analyte is RNA, and the analyte binding arms and the reporter binding arms of the oligonucleotide probe are RNA oligonucleotides.

41. The method of claim 32, wherein the first and second strands are separated by a 5 nucleotide gap.

42. The probe of claim 1, wherein the analyte binding arms each comprise from about 8 to about 10 nucleotides.

\* \* \* \* \*

SEQUENCE LISTING

<160> NUMBER OF SEQ ID NOS: 120

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
ccgagaagtt aagacctatg ctcgg                                              25

<210> SEQ ID NO 2
<211> LENGTH: 12
<212> TYPE: RNA
<213> ORGANISM: Artificial Sequence
<220> FEATURE:
<223> OTHER INFORMATION: Synthetic Construct

<400> SEQUENCE: 2
uuucccgacu gg                                                            12

<210> SEQ ID NO 3
<211> LENGTH: 18
<212> TYPE: RNA
<213> ORGANISM: Artificial Sequence
<220> FEATURE:
<223> OTHER INFORMATION: Synthetic Construct

<400> SEQUENCE: 3
ccagguaacg aauggauu                                                      18

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
ctcgcaccca ctctctccat gcgag                                              25

<210> SEQ ID NO 5
<211> LENGTH: 53
<212> TYPE: DNA
<213> ORGANISM: Artificial Sequence
<220> FEATURE:
<223> OTHER INFORMATION: Synthetic Construct

<400> SEQUENCE: 5
ccaaagaata agcaccggct aactccgtgc cagcagccgc ggtaatacgg ggg               53

<210> SEQ ID NO 6
<211> LENGTH: 40
<212> TYPE: DNA
<213> ORGANISM: Artificial Sequence
<220> FEATURE:
<223> OTHER INFORMATION: Synthetic Construct

<400> SEQUENCE: 6
gccttggggg aggacgttac ccaaagccta agcaccggct                              40

-continued

```
<210> SEQ ID NO 7
<211> LENGTH: 15
<212> TYPE: DNA
<213> ORGANISM: Artificial Sequence
<220> FEATURE:
<223> OTHER INFORMATION: Synthetic Construct

<400> SEQUENCE: 7
ctctctccat gagag                                                        15

<210> SEQ ID NO 8
<211> LENGTH: 15
<212> TYPE: DNA
<213> ORGANISM: Artificial Sequence
<220> FEATURE:
<223> OTHER INFORMATION: Synthetic Construct

<400> SEQUENCE: 8
tgggtctcgc accca                                                        15

<210> SEQ ID NO 9
<211> LENGTH: 36
<212> TYPE: DNA
<213> ORGANISM: Artificial Sequence
<220> FEATURE:
<223> OTHER INFORMATION: Synthetic Construct

<400> SEQUENCE: 9
ccgagccaag ttactcggcc gagatatgag gctcgg                                 36

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
cagcgagtca tagccggtgc                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
cttaaggcac ggagttaggt                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
cgcggctgct cttctcgctg                                                   20

<210> SEQ ID NO 13
<211> LENGTH: 30
<212> TYPE: DNA
<213> ORGANISM: Artificial Sequence
<220> FEATURE:
<223> OTHER INFORMATION: Synthetic Construct

<400> SEQUENCE: 13
```
cagcgagaag ttaagaccta tgactcgctg                                              30

<210> SEQ ID NO 14
<211> LENGTH: 47
<212> TYPE: DNA
<213> ORGANISM: Artificial Sequence
<220> FEATURE:
<223> OTHER INFORMATION: Synthetic Construct

<400> SEQUENCE: 14
ccgagtcaag ttactaacct cgggctgcct agatatgaac atgcagc                           47

<210> SEQ ID NO 15
<211> LENGTH: 47
<212> TYPE: DNA
<213> ORGANISM: Artificial Sequence
<220> FEATURE:
<223> OTHER INFORMATION: Synthetic Construct

<400> SEQUENCE: 15
ttaacccacg ccgaatccta gacgcaaagt cgtctaggat tcggcgt                           47

<210> SEQ ID NO 16
<211> LENGTH: 46
<212> TYPE: DNA
<213> ORGANISM: Artificial Sequence
<220> FEATURE:
<223> OTHER INFORMATION: Synthetic Construct

<400> SEQUENCE: 16
cgtctaggat tcggcgtggg ttaagaagtt aagacctatg tagacg                            46

<210> SEQ ID NO 17
<211> LENGTH: 14
<212> TYPE: DNA
<213> ORGANISM: Artificial Sequence
<220> FEATURE:
<223> OTHER INFORMATION: Synthetic Construct

<400> SEQUENCE: 17
cccccaaggc gggg                                                               14

<210> SEQ ID NO 18
<211> LENGTH: 15
<212> TYPE: DNA
<213> ORGANISM: Artificial Sequence
<220> FEATURE:
<223> OTHER INFORMATION: Synthetic Construct

<400> SEQUENCE: 18
aggacgtaac gtcct                                                              15

<210> SEQ ID NO 19
<211> LENGTH: 16
<212> TYPE: DNA
<213> ORGANISM: Artificial Sequence
<220> FEATURE:
<223> OTHER INFORMATION: Synthetic construct

<400> SEQUENCE: 19
cataggtctt aacttc                                                             16

<210> SEQ ID NO 20
<211> LENGTH: 20
<212> TYPE: DNA
<213> ORGANISM: Artificial Sequence

```
<220> FEATURE:
<223> OTHER INFORMATION: Synthetic construct

<400> SEQUENCE: 20
atgtagagag tgggtgcgag                                              20

<210> SEQ ID NO 21
<211> LENGTH: 54
<212> TYPE: RNA
<213> ORGANISM: Artificial Sequence
<220> FEATURE:
<223> OTHER INFORMATION: Synthetic construct

<400> SEQUENCE: 21
ggaaccucgc uucggcgaug auggagaggc gcaagguuaa ccgccucagg uucc         54

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
atggagagag tgggtgcgag                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
ttggagagag tgggtgcgag                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
agggagagag tgggtgcgag                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
atagagagag tgggtgcgag                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
atggcgagag tgggtgcgag                                              20
```

-continued

```
<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
atggatagag tgggtgcgag                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
atggagggag tgggtgcgag                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
atggagaaag tgggtgcgag                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
atggagagcg tgggtgcgag                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
atggagagat tgggtgcgag                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic construct

<400> SEQUENCE: 32
atggagagag ggggtgcgag                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
```

| | |
|---|---|
| atggagagag taggtgcgag | 20 |

<210> SEQ ID NO 34
<211> LENGTH: 20
<212> TYPE: DNA
<213> ORGANISM: Artificial Sequence
<220> FEATURE:
<223> OTHER INFORMATION: Synthetic construct

<400> SEQUENCE: 34

| | |
|---|---|
| atggagagag tgtgtgcgag | 20 |

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35

| | |
|---|---|
| atggagagag tggttgcgag | 20 |

<210> SEQ ID NO 36
<211> LENGTH: 20
<212> TYPE: DNA
<213> ORGANISM: Artificial Sequence
<220> FEATURE:
<223> OTHER INFORMATION: Synthetic construct

<400> SEQUENCE: 36

| | |
|---|---|
| atggagagag tgggagcgag | 20 |

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37

| | |
|---|---|
| atggagagag tgggttcgag | 20 |

<210> SEQ ID NO 38
<211> LENGTH: 20
<212> TYPE: DNA
<213> ORGANISM: Artificial Sequence
<220> FEATURE:
<223> OTHER INFORMATION: Synthetic construct

<400> SEQUENCE: 38

| | |
|---|---|
| atggagagag tgggtgtgag | 20 |

<210> SEQ ID NO 39
<211> LENGTH: 20
<212> TYPE: DNA
<213> ORGANISM: Artificial Sequence
<220> FEATURE:
<223> OTHER INFORMATION: Synthetic construct

<400> SEQUENCE: 39

| | |
|---|---|
| atggagagag tgggtgccag | 20 |

<210> SEQ ID NO 40
<211> LENGTH: 20
<212> TYPE: DNA
<213> ORGANISM: Artificial Sequence -continued

```
<220> FEATURE:
<223> OTHER INFORMATION: Synthetic construct

<400> SEQUENCE: 40
atggagagag tgggtgcggg                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
atggagagag tgggtgcgaa                                              20

<210> SEQ ID NO 42
<211> LENGTH: 20
<212> TYPE: DNA
<213> ORGANISM: Francisella tularensis

<400> SEQUENCE: 42
gccttggggg aggacgttac                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic construct

<400> SEQUENCE: 43
gctttggggg aggacgttac                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct

<400> SEQUENCE: 44
accttggggg aggacgttac                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
gtcttggggg aggacgttac                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic construct

<400> SEQUENCE: 46
gccttgggga aggacgttac                                              20

<210> SEQ ID NO 47
<211> LENGTH: 20
```

```
<212> TYPE: DNA
<213> ORGANISM: Artificial Sequence
<220> FEATURE:
<223> OTHER INFORMATION: Synthetic construct

<400> SEQUENCE: 47
gccttggggg aggacgttat                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic construct

<400> SEQUENCE: 48
gccttggggg aggatgttac                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic construct

<400> SEQUENCE: 49
gccttggggg aggacgtcac                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic construct

<400> SEQUENCE: 50
gccttgggga gggacgttac                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic construct

<400> SEQUENCE: 51
gtcttgggga aggacgttac                                               20

<210> SEQ ID NO 52
<211> LENGTH: 14
<212> TYPE: DNA
<213> ORGANISM: Artificial Sequence
<220> FEATURE:
<223> OTHER INFORMATION: Synthetic construct

<400> SEQUENCE: 52
gagagagtgg gtgc                                                     14

<210> SEQ ID NO 53
<211> LENGTH: 14
<212> TYPE: DNA
<213> ORGANISM: Artificial Sequence
<220> FEATURE:
<223> OTHER INFORMATION: Synthetic construct

<400> SEQUENCE: 53
aagagagtgg gtgc                                                     14
```

```
<210> SEQ ID NO 54
<211> LENGTH: 14
<212> TYPE: DNA
<213> ORGANISM: Artificial Sequence
<220> FEATURE:
<223> OTHER INFORMATION: Synthetic construct

<400> SEQUENCE: 54
cagagagtgg gtgc                                                        14

<210> SEQ ID NO 55
<211> LENGTH: 14
<212> TYPE: DNA
<213> ORGANISM: Artificial Sequence
<220> FEATURE:
<223> OTHER INFORMATION: Synthetic construct

<400> SEQUENCE: 55
tagagagtgg gtgc                                                        14

<210> SEQ ID NO 56
<211> LENGTH: 14
<212> TYPE: DNA
<213> ORGANISM: Artificial Sequence
<220> FEATURE:
<223> OTHER INFORMATION: Synthetic construct

<400> SEQUENCE: 56
gcgagagtgg gtgc                                                        14

<210> SEQ ID NO 57
<211> LENGTH: 14
<212> TYPE: DNA
<213> ORGANISM: Artificial Sequence
<220> FEATURE:
<223> OTHER INFORMATION: Synthetic construct

<400> SEQUENCE: 57
gggagagtgg gtgc                                                        14

<210> SEQ ID NO 58
<211> LENGTH: 14
<212> TYPE: DNA
<213> ORGANISM: Artificial Sequence
<220> FEATURE:
<223> OTHER INFORMATION: Synthetic construct

<400> SEQUENCE: 58
gtgagagtgg gtgc                                                        14

<210> SEQ ID NO 59
<211> LENGTH: 14
<212> TYPE: DNA
<213> ORGANISM: Artificial Sequence
<220> FEATURE:
<223> OTHER INFORMATION: Synthetic construct

<400> SEQUENCE: 59
gaaagagtgg gtgc                                                        14

<210> SEQ ID NO 60
<211> LENGTH: 14
<212> TYPE: DNA
<213> ORGANISM: Artificial Sequence
<220> FEATURE:
<223> OTHER INFORMATION: Synthetic construct
```

```
<400> SEQUENCE: 60
gacagagtgg gtgc                                                 14

<210> SEQ ID NO 61
<211> LENGTH: 14
<212> TYPE: DNA
<213> ORGANISM: Artificial Sequence
<220> FEATURE:
<223> OTHER INFORMATION: Synthetic construct

<400> SEQUENCE: 61
gatagagtgg gtgc                                                 14

<210> SEQ ID NO 62
<211> LENGTH: 14
<212> TYPE: DNA
<213> ORGANISM: Artificial Sequence
<220> FEATURE:
<223> OTHER INFORMATION: Synthetic construct

<400> SEQUENCE: 62
gagcgagtgg gtgc                                                 14

<210> SEQ ID NO 63
<211> LENGTH: 14
<212> TYPE: DNA
<213> ORGANISM: Artificial Sequence
<220> FEATURE:
<223> OTHER INFORMATION: Synthetic construct

<400> SEQUENCE: 63
gagggagtgg gtgc                                                 14

<210> SEQ ID NO 64
<211> LENGTH: 14
<212> TYPE: DNA
<213> ORGANISM: Artificial Sequence
<220> FEATURE:
<223> OTHER INFORMATION: Synthetic construct

<400> SEQUENCE: 64
gagtgagtgg gtgc                                                 14

<210> SEQ ID NO 65
<211> LENGTH: 14
<212> TYPE: DNA
<213> ORGANISM: Artificial Sequence
<220> FEATURE:
<223> OTHER INFORMATION: Synthetic construct

<400> SEQUENCE: 65
gagaaagtgg gtgc                                                 14

<210> SEQ ID NO 66
<211> LENGTH: 14
<212> TYPE: DNA
<213> ORGANISM: Artificial Sequence
<220> FEATURE:
<223> OTHER INFORMATION: Synthetic construct

<400> SEQUENCE: 66
gagacagtgg gtgc                                                 14

<210> SEQ ID NO 67
<211> LENGTH: 14
```

```
<212> TYPE: DNA
<213> ORGANISM: Artificial Sequence
<220> FEATURE:
<223> OTHER INFORMATION: Synthetic construct

<400> SEQUENCE: 67
gagatagtgg gtgc                                                         14

<210> SEQ ID NO 68
<211> LENGTH: 14
<212> TYPE: DNA
<213> ORGANISM: Artificial Sequence
<220> FEATURE:
<223> OTHER INFORMATION: Synthetic construct

<400> SEQUENCE: 68
gagagcgtgg gtgc                                                         14

<210> SEQ ID NO 69
<211> LENGTH: 14
<212> TYPE: DNA
<213> ORGANISM: Artificial Sequence
<220> FEATURE:
<223> OTHER INFORMATION: Synthetic construct

<400> SEQUENCE: 69
gagagggtgg gtgc                                                         14

<210> SEQ ID NO 70
<211> LENGTH: 14
<212> TYPE: DNA
<213> ORGANISM: Artificial Sequence
<220> FEATURE:
<223> OTHER INFORMATION: Synthetic construct

<400> SEQUENCE: 70
gagagtgtgg gtgc                                                         14

<210> SEQ ID NO 71
<211> LENGTH: 14
<212> TYPE: DNA
<213> ORGANISM: Artificial Sequence
<220> FEATURE:
<223> OTHER INFORMATION: Synthetic construct

<400> SEQUENCE: 71
gagagaatgg gtgc                                                         14

<210> SEQ ID NO 72
<211> LENGTH: 14
<212> TYPE: DNA
<213> ORGANISM: Artificial Sequence
<220> FEATURE:
<223> OTHER INFORMATION: Synthetic construct

<400> SEQUENCE: 72
gagagactgg gtgc                                                         14

<210> SEQ ID NO 73
<211> LENGTH: 14
<212> TYPE: DNA
<213> ORGANISM: Artificial Sequence
<220> FEATURE:
<223> OTHER INFORMATION: Synthetic construct

<400> SEQUENCE: 73
gagagattgg gtgc                                                         14
```

<210> SEQ ID NO 74
<211> LENGTH: 14
<212> TYPE: DNA
<213> ORGANISM: Artificial Sequence
<220> FEATURE:
<223> OTHER INFORMATION: Synthetic construct

<400> SEQUENCE: 74
gagagagagg gtgc                                                        14

<210> SEQ ID NO 75
<211> LENGTH: 14
<212> TYPE: DNA
<213> ORGANISM: Artificial Sequence
<220> FEATURE:
<223> OTHER INFORMATION: Synthetic construct

<400> SEQUENCE: 75
gagagagcgg gtgc                                                        14

<210> SEQ ID NO 76
<211> LENGTH: 14
<212> TYPE: DNA
<213> ORGANISM: Artificial Sequence
<220> FEATURE:
<223> OTHER INFORMATION: Synthetic construct

<400> SEQUENCE: 76
gagagagggg gtgc                                                        14

<210> SEQ ID NO 77
<211> LENGTH: 14
<212> TYPE: DNA
<213> ORGANISM: Artificial Sequence
<220> FEATURE:
<223> OTHER INFORMATION: Synthetic construct

<400> SEQUENCE: 77
gagagagtag gtgc                                                        14

<210> SEQ ID NO 78
<211> LENGTH: 14
<212> TYPE: DNA
<213> ORGANISM: Artificial Sequence
<220> FEATURE:
<223> OTHER INFORMATION: Synthetic construct

<400> SEQUENCE: 78
gagagagtcg gtgc                                                        14

<210> SEQ ID NO 79
<211> LENGTH: 14
<212> TYPE: DNA
<213> ORGANISM: Artificial Sequence
<220> FEATURE:
<223> OTHER INFORMATION: Synthetic construct

<400> SEQUENCE: 79
gagagagttg gtgc                                                        14

<210> SEQ ID NO 80
<211> LENGTH: 14
<212> TYPE: DNA
<213> ORGANISM: Artificial Sequence
<220> FEATURE:
<223> OTHER INFORMATION: Synthetic construct -continued

<400> SEQUENCE: 80
gagagagtga gtgc                                                    14

<210> SEQ ID NO 81
<211> LENGTH: 14
<212> TYPE: DNA
<213> ORGANISM: Artificial Sequence
<220> FEATURE:
<223> OTHER INFORMATION: Synthetic construct

<400> SEQUENCE: 81
gagagagtgc gtgc                                                    14

<210> SEQ ID NO 82
<211> LENGTH: 14
<212> TYPE: DNA
<213> ORGANISM: Artificial Sequence
<220> FEATURE:
<223> OTHER INFORMATION: Synthetic construct

<400> SEQUENCE: 82
gagagagtgt gtgc                                                    14

<210> SEQ ID NO 83
<211> LENGTH: 14
<212> TYPE: DNA
<213> ORGANISM: Artificial Sequence
<220> FEATURE:
<223> OTHER INFORMATION: Synthetic construct

<400> SEQUENCE: 83
gagagagtgg atgc                                                    14

<210> SEQ ID NO 84
<211> LENGTH: 14
<212> TYPE: DNA
<213> ORGANISM: Artificial Sequence
<220> FEATURE:
<223> OTHER INFORMATION: Synthetic construct

<400> SEQUENCE: 84
gagagagtgg ctgc                                                    14

<210> SEQ ID NO 85
<211> LENGTH: 14
<212> TYPE: DNA
<213> ORGANISM: Artificial Sequence
<220> FEATURE:
<223> OTHER INFORMATION: Synthetic construct

<400> SEQUENCE: 85
gagagagtgg ttgc                                                    14

<210> SEQ ID NO 86
<211> LENGTH: 14
<212> TYPE: DNA
<213> ORGANISM: Artificial Sequence
<220> FEATURE:
<223> OTHER INFORMATION: Synthetic construct

<400> SEQUENCE: 86
gagagagtgg gagc                                                    14

<210> SEQ ID NO 87
<211> LENGTH: 14

```
<212> TYPE: DNA
<213> ORGANISM: Artificial Sequence
<220> FEATURE:
<223> OTHER INFORMATION: Synthetic construct

<400> SEQUENCE: 87
gagagagtgg gcgc                                                       14

<210> SEQ ID NO 88
<211> LENGTH: 14
<212> TYPE: DNA
<213> ORGANISM: Artificial Sequence
<220> FEATURE:
<223> OTHER INFORMATION: Synthetic construct

<400> SEQUENCE: 88
gagagagtgg gggc                                                       14

<210> SEQ ID NO 89
<211> LENGTH: 14
<212> TYPE: DNA
<213> ORGANISM: Artificial Sequence
<220> FEATURE:
<223> OTHER INFORMATION: Synthetic construct

<400> SEQUENCE: 89
gagagagtgg gtac                                                       14

<210> SEQ ID NO 90
<211> LENGTH: 14
<212> TYPE: DNA
<213> ORGANISM: Artificial Sequence
<220> FEATURE:
<223> OTHER INFORMATION: Synthetic construct

<400> SEQUENCE: 90
gagagagtgg gtcc                                                       14

<210> SEQ ID NO 91
<211> LENGTH: 14
<212> TYPE: DNA
<213> ORGANISM: Artificial Sequence
<220> FEATURE:
<223> OTHER INFORMATION: Synthetic construct

<400> SEQUENCE: 91
gagagagtgg gttc                                                       14

<210> SEQ ID NO 92
<211> LENGTH: 14
<212> TYPE: DNA
<213> ORGANISM: Artificial Sequence
<220> FEATURE:
<223> OTHER INFORMATION: Synthetic construct

<400> SEQUENCE: 92
gagagagtgg gtga                                                       14

<210> SEQ ID NO 93
<211> LENGTH: 14
<212> TYPE: DNA
<213> ORGANISM: Artificial Sequence
<220> FEATURE:
<223> OTHER INFORMATION: Synthetic construct

<400> SEQUENCE: 93
gagagagtgg gtgg                                                       14
```

```
<210> SEQ ID NO 94
<211> LENGTH: 14
<212> TYPE: DNA
<213> ORGANISM: Artificial Sequence
<220> FEATURE:
<223> OTHER INFORMATION: Synthetic construct

<400> SEQUENCE: 94
gagagagtgg gtgt                                                        14

<210> SEQ ID NO 95
<211> LENGTH: 19
<212> TYPE: RNA
<213> ORGANISM: Artificial Sequence
<220> FEATURE:
<223> OTHER INFORMATION: Synthetic construct

<400> SEQUENCE: 95
gcacccauuu cccgacugg                                                   19

<210> SEQ ID NO 96
<211> LENGTH: 25
<212> TYPE: RNA
<213> ORGANISM: Artificial Sequence
<220> FEATURE:
<223> OTHER INFORMATION: Synthetic construct

<400> SEQUENCE: 96
ccagguaacg aauggauucu cucuc                                            25

<210> SEQ ID NO 97
<211> LENGTH: 15
<212> TYPE: DNA
<213> ORGANISM: Artificial Sequence
<220> FEATURE:
<223> OTHER INFORMATION: Synthetic construct

<400> SEQUENCE: 97
gagagagttg ggtgc                                                       15

<210> SEQ ID NO 98
<211> LENGTH: 16
<212> TYPE: DNA
<213> ORGANISM: Artificial Sequence
<220> FEATURE:
<223> OTHER INFORMATION: Synthetic construct

<400> SEQUENCE: 98
gagagagttt gggtgc                                                      16

<210> SEQ ID NO 99
<211> LENGTH: 10
<212> TYPE: DNA
<213> ORGANISM: Artificial Sequence
<220> FEATURE:
<223> OTHER INFORMATION: Synthetic construct

<400> SEQUENCE: 99
ctctctccat                                                             10

<210> SEQ ID NO 100
<211> LENGTH: 10
<212> TYPE: DNA
<213> ORGANISM: Artificial Sequence
<220> FEATURE:
<223> OTHER INFORMATION: Synthetic construct
```

```
<400> SEQUENCE: 100
ctcgcaccca                                                            10

<210> SEQ ID NO 101
<211> LENGTH: 38
<212> TYPE: RNA
<213> ORGANISM: Artificial Sequence
<220> FEATURE:
<223> OTHER INFORMATION: Synthetic construct

<400> SEQUENCE: 101
ggaucccgac uggcgagagc cagguaacga auggaucc                             38

<210> SEQ ID NO 102
<211> LENGTH: 21
<212> TYPE: DNA
<213> ORGANISM: Artificial Sequence
<220> FEATURE:
<223> OTHER INFORMATION: Synthetic construct

<400> SEQUENCE: 102
gagttagccg gtgcttattc t                                               21

<210> SEQ ID NO 103
<211> LENGTH: 21
<212> TYPE: DNA
<213> ORGANISM: Artificial Sequence
<220> FEATURE:
<223> OTHER INFORMATION: Synthetic construct

<400> SEQUENCE: 103
cccgtattac cgcggctgct g                                               21

<210> SEQ ID NO 104
<211> LENGTH: 52
<212> TYPE: DNA
<213> ORGANISM: Artificial Sequence
<220> FEATURE:
<223> OTHER INFORMATION: Synthetic construct

<400> SEQUENCE: 104
ccaaagaata agcaccggct aactccggcc agcagccgcg gtaatacggg gg             52

<210> SEQ ID NO 105
<211> LENGTH: 53
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (28)..(28)
<223> OTHER INFORMATION: n is a, c, g, or t

<400> SEQUENCE: 105
ccaaagaata agcaccggct aactccgngc cagcagccgc ggtaatacgg ggg            53

<210> SEQ ID NO 106
<211> LENGTH: 54
<212> TYPE: DNA
<213> ORGANISM: Artificial Sequence
<220> FEATURE:
<223> OTHER INFORMATION: Synthetic construct

<400> SEQUENCE: 106
ccaaagaata agcaccggct aactccgttg ccagcagccg cggtaatacg gggg           54
```

<210> SEQ ID NO 107
<211> LENGTH: 16
<212> TYPE: DNA
<213> ORGANISM: Artificial Sequence
<220> FEATURE:
<223> OTHER INFORMATION: Synthetic construct

<400> SEQUENCE: 107
cgtcctcccc caaggc                                                             16

<210> SEQ ID NO 108
<211> LENGTH: 18
<212> TYPE: DNA
<213> ORGANISM: Artificial Sequence
<220> FEATURE:
<223> OTHER INFORMATION: Synthetic construct

<400> SEQUENCE: 108
gccggtggtt attctttg                                                           18

<210> SEQ ID NO 109
<211> LENGTH: 19
<212> TYPE: DNA
<213> ORGANISM: Artificial Sequence
<220> FEATURE:
<223> OTHER INFORMATION: Synthetic construct

<400> SEQUENCE: 109
ccgagcctca tatcctcgg                                                          19

<210> SEQ ID NO 110
<211> LENGTH: 18
<212> TYPE: DNA
<213> ORGANISM: Artificial Sequence
<220> FEATURE:
<223> OTHER INFORMATION: Synthetic construct

<400> SEQUENCE: 110
ccgagtaact tggctcgg                                                           18

<210> SEQ ID NO 111
<211> LENGTH: 17
<212> TYPE: DNA
<213> ORGANISM: Artificial Sequence
<220> FEATURE:
<223> OTHER INFORMATION: Synthetic construct

<400> SEQUENCE: 111
ccgagcctca tatctgg                                                            17

<210> SEQ ID NO 112
<211> LENGTH: 35
<212> TYPE: DNA
<213> ORGANISM: Artificial Sequence
<220> FEATURE:
<223> OTHER INFORMATION: Synthetic construct

<400> SEQUENCE: 112
ccgagccaag ttactcggcc agatatgagg ctcgg                                        35

<210> SEQ ID NO 113
<211> LENGTH: 30
<212> TYPE: DNA
<213> ORGANISM: Artificial Sequence
<220> FEATURE:
<223> OTHER INFORMATION: Synthetic construct

<400> SEQUENCE: 113
gcaccggcta actccgtgcc agcagccgcg                                    30

<210> SEQ ID NO 114
<211> LENGTH: 17
<212> TYPE: DNA
<213> ORGANISM: Artificial Sequence
<220> FEATURE:
<223> OTHER INFORMATION: Synthetic construct

<400> SEQUENCE: 114
gctgcatgaa gctgctt                                                  17

<210> SEQ ID NO 115
<211> LENGTH: 20
<212> TYPE: DNA
<213> ORGANISM: Artificial Sequence
<220> FEATURE:
<223> OTHER INFORMATION: Synthetic construct

<400> SEQUENCE: 115
atctaacccc aactattcat                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic construct

<400> SEQUENCE: 116
tttccggcag cccgagaggc                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic construct

<400> SEQUENCE: 117
attggttcca attatcaatg                                               20

<210> SEQ ID NO 118
<211> LENGTH: 17
<212> TYPE: DNA
<213> ORGANISM: Artificial Sequence
<220> FEATURE:
<223> OTHER INFORMATION: Synthetic construct

<400> SEQUENCE: 118
cccaacgctt gactcgg                                                  17

<210> SEQ ID NO 119
<211> LENGTH: 52
<212> TYPE: DNA
<213> ORGANISM: Artificial Sequence
<220> FEATURE:
<223> OTHER INFORMATION: Synthetic construct

<400> SEQUENCE: 119
gtaaagcact ttagttgggg aggaaagcct caaggttaat agccttgggg ga           52

<210> SEQ ID NO 120
<211> LENGTH: 48

-continued

```
<212> TYPE: DNA
<213> ORGANISM: Artificial Sequence
<220> FEATURE:
<223> OTHER INFORMATION: Synthetic construct

<400> SEQUENCE: 120
ttaacccacg ccgaatccta gacgcaaagt cgtctaggat tcggcgtg           48
```